United States Patent
Mensonides-Harsema et al.

(10) Patent No.: US 12,274,706 B2
(45) Date of Patent: *Apr. 15, 2025

(54) PHARMACEUTICAL COMPOSITION FOR ORAL ADMINISTRATION CONTAINING SULFASALAZINE AND/OR A SULFASALAZINE ORGANIC SALT, PRODUCTION PROCESS AND USE

(71) Applicant: MEDAC GESELLSCHAFT FUER KLINISCHE SPEZIALPRAEPARATE MBH, Wedel (DE)

(72) Inventors: Marguerite Mensonides-Harsema, Houston, TX (US); Sebastian Bialleck, Wedel (DE); Sonja Schuldt-Lieb, Wedel (DE)

(73) Assignee: MEDAC GESELLSCHAFT FUER KLINISCHE (DE)

(*) Notice: Subject to any disclaimer, the term of this patent is extended or adjusted under 35 U.S.C. 154(b) by 79 days.

This patent is subject to a terminal disclaimer.

(21) Appl. No.: 18/201,106

(22) Filed: May 23, 2023

(65) Prior Publication Data
US 2023/0381203 A1 Nov. 30, 2023

Related U.S. Application Data

(62) Division of application No. 16/766,665, filed as application No. PCT/EP2018/082331 on Nov. 23, 2018, now Pat. No. 11,690,857.

(30) Foreign Application Priority Data

Nov. 23, 2017 (EP) .................. 17203276

(51) Int. Cl.
| | | |
|---|---|---|
| A61K 31/655 | (2006.01) | |
| A61K 9/00 | (2006.01) | |
| A61K 9/20 | (2006.01) | |
| A61K 9/28 | (2006.01) | |
| A61K 9/48 | (2006.01) | |
| A61K 9/50 | (2006.01) | |
| A61K 31/192 | (2006.01) | |
| A61K 31/405 | (2006.01) | |
| A61K 31/415 | (2006.01) | |
| A61K 31/42 | (2006.01) | |
| A61K 31/519 | (2006.01) | |
| A61K 31/5415 | (2006.01) | |
| A61K 31/58 | (2006.01) | |
| A61K 31/616 | (2006.01) | |
| A61K 33/242 | (2019.01) | |
| A61K 39/395 | (2006.01) | |

(52) U.S. Cl.
CPC .......... *A61K 31/655* (2013.01); *A61K 9/0053* (2013.01); *A61K 9/2095* (2013.01); *A61K 9/2886* (2013.01); *A61K 9/2893* (2013.01); *A61K 9/4808* (2013.01); *A61K 9/4833* (2013.01); *A61K 9/5089* (2013.01); *A61K 31/192* (2013.01); *A61K 31/405* (2013.01); *A61K 31/415* (2013.01); *A61K 31/42* (2013.01); *A61K 31/519* (2013.01); *A61K 31/5415* (2013.01); *A61K 31/58* (2013.01); *A61K 31/616* (2013.01); *A61K 33/242* (2019.01); *A61K 39/3955* (2013.01)

(58) Field of Classification Search
CPC ..................... A61K 31/4402; A61K 31/655
See application file for complete search history.

(56) References Cited

U.S. PATENT DOCUMENTS

| | | | |
|---|---|---|---|
| 2,396,145 A | 3/1946 | Askeloef | ................ 260/156 |
| 10,703,723 B2 | 7/2020 | Mensonides-Harsema | ................ A61P 37/00 |
| 11,304,936 B2 * | 4/2022 | Mensonides-Harsema | ................ A61K 9/0031 |
| 2006/0045865 A1 | 3/2006 | Jacob et al. | ............ 424/78.27 |
| 2020/0392084 A1 | 12/2020 | Abu-Izza et al. | ..... C07D 213/76 |

FOREIGN PATENT DOCUMENTS

| | | | |
|---|---|---|---|
| CN | 106279008 | 1/2017 | .......... C07D 213/76 |
| EP | 1101490 | 5/2001 | .............. A61K 9/30 |
| GB | 564990 | 10/1944 | |
| GB | 1166684 | 10/1969 | ............ C09B 43/00 |
| JP | 2000-103732 | 4/2000 | ............... A61K 9/30 |
| JP | 2020-536945 | 12/2020 | .......... C07D 213/76 |
| WO | WO9722596 | 6/1997 | .......... C07D 239/94 |
| WO | WO9730035 | 8/1997 | .......... C07D 239/94 |
| WO | WO9732856 | 9/1997 | .......... C07D 239/94 |
| WO | WO9813354 | 4/1998 | .......... C07D 239/94 |
| WO | WO9902166 | 1/1999 | ............ A61K 31/66 |
| WO | WO0040529 | 7/2000 | .......... C07C 13/547 |
| WO | WO0041669 | 7/2000 | |

(Continued)

OTHER PUBLICATIONS

U.S. Appl. No. 16/766,665, filed May 22, 2020.
U.S. Appl. No. 16/766,660, filed May 22, 2020, Mensonides-Harsema.
International Search Report and Written Opinion issued in PCT/EP2018/082330, dated Feb. 22, 2019, pages.
International Preliminary Report on Patentability issued in PCT/EP2018/082330, dated May 26, 2020, pages.
International Search Report and Written Opinion issued in PCT/EP2018/082331, dated Mar. 11, 2019, pages.
International Preliminary Report on Patentability issued in PCT/EP2018/082331, dated May 26, 2020,.

(Continued)

*Primary Examiner* — Rei Tsang Shiao
(74) *Attorney, Agent, or Firm* — HAYBES SOLOWAY P.C.

(57) ABSTRACT

Disclosed is a new pharmaceutical composition for oral administration containing sulfasalazine and/or a sulfasalazine organic salt, production processes and uses, in particular in the treatment of a disease or condition in which modulation of inflammatory cells is beneficial, a disease or condition concerning bones or joints and/or the gastrointestinal tract.

14 Claims, 4 Drawing Sheets

(56) References Cited

FOREIGN PATENT DOCUMENTS

| WO | WO0192224 | 12/2001 | ........... C07D 209/42 |
|----|-----------|---------|-------------------------|
| WO | WO0204434 | 1/2002  | ........... C07D 295/16 |
| WO | WO0208213 | 1/2002  | ......... C07D 295/185  |

OTHER PUBLICATIONS

International Pharmaceutical Excipients Council Japan, Kaitei Iyakuhin Tenkabutsu Handobukku, 2007, pp. 964-966.

Anderson et al., Technomics, Inc., Sep. 25, 1999, pp. 347-365.

Clegg et al., "Comparison of sulfasalazine and placebo in the treatment of psoriatic arthritis: A Department of Veterans Affairs Cooperative Study" *Arthritis & Rheumatism*, 1996, 2 pages.

Couto D. et al, "Scavenging of reactive oxygen and nitrogen species by the prodrug sulfasalazine and its metabolites 5-aminosalicylic acid and sulfapyridine." Redox Report. 2010;15(6):259-67. doi: 10.1179/135100010X12826446921707, abstract only, 2 pages.

Matasic R, et al., "Maturation of Human Dendritic Cells as Sulfasalazine Target."; Croatian Medical Journal, Aug. 2001; 42(4): 440-445, 6 pages.

P Gadangi, et al.; "The anti-inflammatory mechanism of sulfasalazine is related to adenosine release at inflamed sites.", Journal of Immunology, Mar. 1, 1996, 156 (5) 1937-1941, abstract only, 3 pages.

Nygard, B.; Olofsson, J. and Sandberg, M.: "Some physico-chemical properties of salicylazosulphapyridine, including its solubility, protolytic constants and general spectrochemical and Polarographic behavior.", Acta Pharmaceutica Suecica 3: 313-342, Jul. 13, 1966, 30 pages.

Mohamed et al.; "Structural and Thermal Characterization of Cerium, Thorium and Uranyl Complexes of Sulfasalazine" Spectrochimica Acta Part A Molecular Biomolecular Spectroscopy 62 (4-5), 1095-1101. Jun. 13, 2005, abstract only, 2 pages.

Lindbergh Ed, Clary David: "ESCA applied to liquids. ESCA spectra from molecular ions in solution", Chemical Physics Letters, Elsevier BV, NL, vol. 39, No. 1, Apr. 1, 1976, pp. 8-10, XP 009503440.

Dahan et al; "Small intestinal efflux mediated by MRP2 and BCRP shifts sulfasalazine intestinal permeability from high to low, enabling its colonic targeting"; American Journal of Physiology—Gastrointestinal and Liver Physiology Published 2009 vol. 297 No. 2, G371-G377, 7 pages.

Liang et al.; "Evaluation of an accelerated Caco-2 cell permeability model."; J Pharm Sci. Mar. 2000; 89(3): 336-45, abstract only, 2 pages.

Office Action issued in U.S. Appl. No. 16/766,660, dated Oct. 29, 2021, 9 pages.

Office Action issued in U.S. Appl. No. 16/766,660, dated Aug. 26, 2021, 8 pages.

Notice of Allowance issued in U.S. Appl. No. 16/766,660, dated Jan. 26, 2022, 9 pages.

\* cited by examiner

PHARMACEUTICAL COMPOSITION FOR ORAL ADMINISTRATION CONTAINING SULFASALAZINE AND/OR A SULFASALAZINE ORGANIC SALT, PRODUCTION PROCESS AND USE

CROSS REFERENCE TO RELATED APPLICATION

The present application is a divisional patent application of U.S. patent application Ser. No. 16/766,665, filed May 22, 2020, (now U.S. Pat. No. 11,690,857 granted Jun. 14, 2023), which claims benefit to PCT International Patent Application Serial No. PCT/EP2018/082331, filed Nov. 23, 2018, which claims priority from European Patent Application Serial No. 17203276.5, filed Nov. 23, 2017, the contents of which have been incorporated herein by reference.

TECHNICAL FIELD

The present invention relates to a new pharmaceutical composition for oral administration containing sulfasalazine and/or a sulfasalazine organic salt, production processes and uses, in particular in the treatment of a disease or condition in which modulation of inflammatory cells is beneficial, a disease or condition concerning bones or joints and/or the gastro-intestinal tract.

BACKGROUND OF THE INVENTION

The compound known under the generic name sulfasalazine (also known as (3Z)-6-oxo-3-[[4-(pyridin-2-ylsulfamoyl)phenyl]hydrazinylidene]cyclohexa-1,4-diene-1-carboxylic acid (IUPAC); 2-hydroxy-5-[2-[4-[(2-pyridinylamino)sulfonyl]phenyl]diazenyl]-benzoic acid (CA index name)) was first described in U.S. Pat. No. 2,396,145 (GB 564990) and is highly effective in the treatment of different autoimmune diseases, e.g. rheumatoid arthritis, juvenile idiopathic arthritis, ankylosing spondylitis, ulcerative colitis and Crohn's disease.

Sulfasalazine forms brownish-yellow crystals (molecular weight 398.39 g/mol). The melting point is specified with 240° C. to 245° C. (U.S. Pat. No. 2,396,145). The solubility of sulfasalazine in water is less than 5 mg/100 ml. The substance has four theoretical $pk_{a/b}$ values, which are at 0.6, 2.4, 9.7 and 11.8. It has been proven to be very difficult to produce hydrate- and solvate-free salts of sulfasalazine by using established methods.

The structure of sulfasalazine ((3Z)-6-oxo-3-[[4-(pyridin-2-ylsulfamoyl)phenyl]hydrazinylidene]cyclohexa-1,4-diene-1-carboxylic acid (IUPAC); 2-hydroxy-5-[2-[4-[(2-pyridinylamino)sulfonyl]phenyl]diazenyl]-benzoic acid (CA index name)) is shown below:

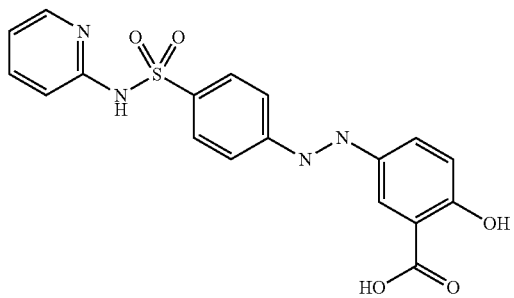 [SMILES: O=C(O)c1cc(NNc2ccc(S(=O)(=O)Nc3ccccn3)cc2)ccc1O]

Sulfasalazine is a well-established active pharmaceutical ingredient and used in anti-inflammatory therapy. Sulfasalazine is used in the treatment of active rheumatoid arthritis, the treatment of active juvenile idiopathic oligoarthritis, the treatment of active juvenile idiopathic polyarthritis and spondyloarthropathy with peripheral arthritis in humans. Sulfasalazine is further used as a prodrug of 5-aminosalicylic acid in the treatment of inflammatory bowel diseases such as Crohn's disease and ulcerative colitis. In adults, guided by tolerability to and efficacy of, sulfasalazine is generally administered orally as tablets at doses of 500-4000 mg per day.

Sulfasalazine is one of the most widely used disease-modifying antirheumatic drugs (DMARD) and is also used in combination with glucocorticoids and/or in combination with other small molecule DMARDs such as methotrexate and/or hydroxychloroquine and/or biological DMARDs such as TNF-alpha relevant biologics.

The mechanism of action of sulfasalazine and its metabolites 5-aminosalicylic acid and sulfapyridine is partially still unknown. Sulfasalazine and/or its metabolites have anti-inflammatory and immune modulating properties in vivo and in vitro at a variety of (inflammatory) cell types such as T-cells, dendritic cells, macrophages, natural killer cells, epithelial cells, B-cells and mast cells through different biological "pathways". It has been shown, for example, that sulfasalazine-treated dendritic cells cannot stimulate T-cells through inhibition of the NF-kB pathway (Matasic R et al 2001, 42, 440-445). In addition it has been demonstrated that sulfasalazine inhibits the binding of TNF-alpha to its receptor in 125I-TNF-alpha displacement studies. Furthermore it has been shown, that sulfasalazine, like methotrexate enhances adenosine release through the inhibition of AICAR transformylase and thus diminishes inflammation (P Gadangi, M Longaker, D Naime, R I Levin, P A Recht, M C Montesinos, M T Buckley, G Carlin and B N Cronstein; "The anti-inflammatory mechanism of sulfasalazine is related to adenosine release at inflamed sites.", J Immunol Mar. 1, 1996, 156 (5) 1937-1941). The well-established antioxidant effects of sulfasalazine in association to its inhibitory effects over neutrophil oxidative burst have been shown to be exerted both through its scavenging effects against reactive oxygen and nitrogen species as well as its metal chelating properties (Couto D1, Ribeiro D, Freitas M, Gomes A, Lima J L, Fernandes E., Redox Rep. 2010; 15(6):259-67. doi: 10.1179/135100010X12826446921707, "Scavenging of reactive oxygen and nitrogen species by the prodrug sulfasalazine and its metabolites 5-aminosalicylic acid and sulfapyridine.").

However, due to the low solubility of sulfasalazine (0.03 mg/mL in de-ionized water at 24° C.) and the current known pharmaceutical compositions of sulfasalazine the systemic bioavailability of sulfasalazine in man is low (about 15 to 20% of an oral dose is absorbed in the small intestine) and the pharmacokinetic intra- and inter-variability is high ($C_{max}$ is 4 to 12 hours, with a median peak concentration at 6 hours). Non-absorbed sulfasalazine is transformed by aza-reducing gut flora to 5-aminosalicylic acid (systemic bioavailability from 10 to 30%) and sulfapyridine (systemic bioavailability to about 60%). The metabolites can be detected in blood plasma after about 10 hours. The half-life of intravenously administered sulfasalazine is approximately 7.6±3.6 hours.

Apart from biotransformation of sulfasalazine by the gut flora in the lower intestine, sulfasalazine is also metabolized in the liver to the metabolites 5-aminosalicylic acid and sulfapyridine. In the liver the primary metabolite sulfapyridine is acetylated prior to excretion, wherein the speed is determined by the acetylation phenotype. Therefore, the half-life of sulfapyridine may vary from 10.4 to 14.8 hours (depending on fast or rather slow acetylators).

The most common side reactions associated with sulfasalazine are anorexia, headache, nausea, vomiting, gastric distress, and apparently reversible oligospermia, tiredness, dizziness, fever, asthenia, insomnia and vertigo might also affect the patient during medication with sulfasalazine.

But also gastrointestinal reactions including hepatitis, hepatic failure, pancreatitis, bloody diarrhea, impaired folic acid absorption, impaired digoxin absorption, stomatitis, diarrhea, abdominal pains, and neutropenic enterocolitis might come up during medication.

Also the skin (e.g. skin rash or itching, urtikaria, increased sensitivity to sunlight), the blood/lymphatic system (aplastic anemia, agranulocytosis, leukopenia, megaloblastic (macrocytic) anemia, purpura, thrombocytopenia, hypoprothrombinemia, methemoglobinemia, congenital neutropenia, and myelodysplastic syndrome) or the central nervous system (transverse myelitis, convulsions, meningitis, transient lesions of the posterior spinal column, cauda equina syndrome, Guillain-Barre syndrome, peripheral neuropathy, mental depression, vertigo, hearing loss, insomnia, ataxia, hallucinations, tinnitus, and drowsiness) might be influenced. Occurring hepatobiliary disorders might be hepatotoxicity, including elevated liver function tests (SGOT/AST, SGPT/ALT, GGT, LDH, alkaline phosphatase, bilirubin), jaundice, cholestatic jaundice, cirrhosis, hepatitis cholestatic, cholestasis and possible hepatocellular damage including liver necrosis and liver failure. Some of these cases were fatal.

The low rate of resorption of sulfasalazine is one reason for the high amount of 500 mg sulfasalazine per single solid oral dosage form, which has to be administered to the patient, in order to obtain a sufficient exposure to the drug sulfasalazine and thus obtain sufficient clinical effect. High amounts of drug substance and/or the big size of the tablets, however, result in a poor patient's compliance and unnecessary high rate of adverse events partly due to unfavorable ratios of sulfasalazine and its metabolites in vivo.

In the manufacture of pharmaceutical compositions, it is important that the active compound is in a form in which it can be conveniently handled and processed in order to obtain a commercially-viable manufacturing process. In this connection, the chemical stability and the physical stability of the active compound are important factors. The active compound, and compositions containing it, must be capable of being effectively stored over appreciable periods of time, without exhibiting any significant change in the physicochemical characteristics (e.g. chemical composition, density, water content and solubility) of the active compound.

Thus, it would be beneficial to provide a solvate free crystal form of sulfasalazine exhibiting solubility properties. From prior art it has become evident that it is very difficult to produce and/or isolate solvate-free crystals of sulfasalazine with simultaneous improved properties like solubility.

It is known, that sulfasalazine has metal chelating properties in vivo. However, the mono salts of sulfasalazine with counterions sodium and potassium, although mentioned in (Nygard, B.; Olofsson, J. and Sandberg, M.: "Some physicochemical properties of salicylazosulphapyridine, including its solubility, protolytic constants and general spectrochemical and Polarographic behavior.", Acta Pharmaceutica Suecica 3: 313-342 (1966)) have never been isolated. The hemi salts of sulfasalazine with metal counterions like strontium (as its trihydrate), calcium (as its trihydrate), magnesium (as its trihydrate) are less soluble than sulfasalazine. Other metal complexes (cerium, thorium and uran) of sulfasalazine with ammonium have been examined as well (G G Mohamed et al. Spectrochim Acta A Mol Biomol Spectrosc 62 (4-5), 1095-1101. 2005 Jun. 13; "Structural and Thermal Characterization of Cerium, Thorium and Uranyl Complexes of Sulfasalazine").

Conformational analysis of sulfasalazine salts with different counter ions like Mg, Sr, Ca and Zn shows that the terminal pyridine ring displays some oriental flexibility, which indicates a propensity for conformational polymorphism of sulfasalazine salts.

Patent application GB 1,166,684 discloses alkoxy-amine addition salts of sulfasalazine. According to the patent the prepared alkoxy-amine addition salts of sulfasalazine are difficult to crystallize in that they are obtained as viscous oils which only crystallize upon stirring with ether or alcohol; a number of the disclosed salts are very hygroscopic and/or have a high water content. For example, the N-methl-(1)-D-glucosamine salt (also known as meglumine salt, which is used hereinafter) of sulfasalazine identified in GB 1,166,684 and prepared by adding a solution of methylglucamine in hot methylglycol to a solution of sulfasalazine in 2-methoxyethanol, exhibits, after extensive drying, a water content of 9%. Such a moisture content is in particular unsuitable for producing stable pharmaceutical compositions.

Due to their unfavorable physicochemical characteristics (hygroscopicity and/or high water content and/or poor solubility and/or pharmaceutical unacceptability) none of the prior disclosed sulfasalazine salts have been considered suitable for the use in pharmaceutical compositions.

CN 106 279 008 A relates to the technical field of purification process of sulfasalazine (5-[p-(2-pyridylaminosulfonyl)benzene]azo-salicylic acid. Sulfasalazine is purified by using specific amine salts of sulfasalazine as intermediate products and precipitating sulfasalazine from a solution containing the specific amine salt. According to example 6, a specific diethylamine salt of sulfasalazine is prepared as intermediate product and the sulfasalazine is subsequently precipitated from the solution. The applicant has prepared the diethylamine salt sulfasalazine intermediate in accordance with the description as provided in example 6 of CN 106 279 008 A. In addition the resulting diethylamine salt of sulfasalazine has been evaluated by an X-ray powder diffractogram (XRPD), which proved that the resulting diethylamine sulfasalazine product is present as crystal Form A of the diethylamine salt of sulfasalazine according to FIG. 3.

Thus, there is still a need to provide a pharmaceutical composition of sulfasalazine with an increased bioavailability of sulfasalazine and/or solubility of sulfasalazine and/or improved risk-benefit ratio of the pharmaceutical sulfasalazine composition, in particular due to a decreased degree of adverse events and/or an improved patient compliance.

BRIEF DESCRIPTION OF THE INVENTION

Accordingly, a first aspect of the present invention relates to a process for preparing a pharmaceutical composition for oral administration comprising 2-hydroxy-5-[2-[4-[(2-pyridinylamino)sulfonyl]phenyl]diazenyl]-benzoic acid (sulfasalazine) and/or a sulfasalazine organic salt, the process comprising or consisting of the following steps:

A: Providing sulfasalazine,
B: Providing an organic amine containing constituent, preferably selected from meglumine piperazine and diethylamine, C: Providing one or more pharmaceutical excipients and optionally one or more further active ingredients, D: Mixing a therapeutically effective amount of sulfasalazine of step A) with a suitable amount of the organic amine containing constituent of step B) and the one or more pharmaceutical excipients and optionally one or more further active ingredient of step C) to form the pharmaceutical composition for oral administration, wherein the organic amine containing constituent does not represent Tris(hydroxymethyl)aminomethane (Tromethane Base).

A second aspect of the present invention relates to a pharmaceutical composition for oral administration obtainable according to an inventive preparation process.

A third aspect of the present invention relates to an inventive pharmaceutical composition for use in the treatment of i) A human disease or condition in which modulation of inflammatory cells is beneficial, ii) A disease or condition concerning bones or joints, preferably selected from the group consisting of arthritis associated with or including osteoarthritis/osteoarthrosis, both primary and secondary to, for example, congenital hip dysplasia; cervical and lumbar spondylitis, and low back and neck pain; rheumatoid arthritis and Still's disease; seronegative spondyloarthropathies including ankylosing spondylitis, psoriatic arthritis, reactive arthritis and undifferentiated spondarthropathy, septic arthritis and other infection-related arthopathies and bone disorders such as tuberculosis, including Potts' disease and Poncet's syndrome; acute and chronic crystal-induced synovitis including urate gout, calcium pyrophosphate deposition disease, and calcium apatite related tendon, bursal and synovial inflammation; Behcet's disease; primary and secondary Sjogren's syndrome; systemic sclerosis and limited scleroderma; systemic lupus erythematosus, mixed connective tissue disease, and undifferentiated connective tissue disease; inflammatory myopathies including dermatomyositis and polymyositis; polymyalgia rheumatic; juvenile arthritis including idiopathic inflammatory arthritis of whatever joint distribution and associated syndromes, and rheumatic fever and its systemic complications; vasculitis including giant cell arteritis, Takayasu's arteritis, Churg-Strauss syndrome, polyarteritis nodos, microscopic polyarteritis, and vasculitis associated with viral infection, hypersensitivity reactions, cryoglobulins, and paraproteins; low back pain; Familial Mediterranean fever, Muckle-Wells syndrome, and Familial Hibernian Fever, Kikuchi disease; drug-induced arthralgias, tendonitis, and myopathies; and iii) A disease or condition concerning gastro-intestinal tract, preferably selected from the group consisting of eosinophilic gastro-enteritis, mastocytosis, Crohn's disease, colitis including ulcerative colitis, proctitis; coeliac disease, irritable bowel syndrome, and food-related allergies which may have effects remote from the gut, e.g. migraine, rhinitis or eczema.

A fourth aspect of the present invention relates to the use of an inventive pharmaceutical composition in the preparation of a medicament for/in the treatment of i) A human disease or condition in which modulation of inflammatory cells is beneficial, ii) A disease or condition concerning bones or joints, preferably selected from the group consisting of arthritis associated with or including osteoarthritis/osteoarthrosis, both primary and secondary to, for example, congenital hip dysplasia; cervical and lumbar spondylitis, and low back and neck pain; rheumatoid arthritis and Still's disease; seronegative spondyloarthropathies including ankylosing spondylitis, psoriatic arthritis, reactive arthritis and undifferentiated spondarthropathy, septic arthritis and other infection-related arthopathies and bone disorders such as tuberculosis, including Potts' disease and Poncet's syndrome; acute and chronic crystal-induced synovitis including urate gout, calcium pyrophosphate deposition disease, and calcium apatite related tendon, bursal and synovial inflammation; Behcet's disease; primary and secondary Sjogren's syndrome; systemic sclerosis and limited scleroderma; systemic lupus erythematosus, mixed connective tissue disease, and undifferentiated connective tissue disease; inflammatory myopathies including dermatomyositis and polymyositis; polymyalgia rheumatic; juvenile arthritis including idiopathic inflammatory arthritis of whatever joint distribution and associated syndromes, and rheumatic fever and its systemic complications; vasculitis including giant cell arteritis, Takayasu's arteritis, Churg-Strauss syndrome, polyarteritis nodos, microscopic polyarteritis, and vasculitis associated with viral infection, hypersensitivity reactions, cryoglobulins, and paraproteins; low back pain; Familial Mediterranean fever, Muckle-Wells syndrome, and Familial Hibernian Fever, Kikuchi disease; drug-induced arthralgias, tendonitis, and myopathies; and iii) A disease or condition concerning gastro-intestinal tract, preferably selected from the group consisting of eosinophilic gastro-enteritis, mastocytosis, Crohn's disease, colitis including ulcerative colitis, proctitis; coeliac disease, irritable bowel syndrome, and food-related allergies which may have effects remote from the gut, e.g. migraine, rhinitis or eczema.

A fifth aspect of the present invention relates to a method of treating i) A human disease or condition in which modulation of inflammatory cells is beneficial, ii) A disease or condition concerning bones or joints, preferably selected from the group consisting of arthritis associated with or including osteoarthritis/osteoarthrosis, both primary and secondary to, for example, congenital hip dysplasia; cervical and lumbar spondylitis, and low back and neck pain; rheumatoid arthritis and Still's disease; seronegative spondyloarthropathies including ankylosing spondylitis, psoriatic arthritis, reactive arthritis and undifferentiated spondarthropathy, septic arthritis and other infection-related arthopathies and bone disorders such as tuberculosis, including Potts' disease and Poncet's syndrome; acute and chronic crystal-induced synovitis including urate gout, calcium pyrophosphate deposition disease, and calcium apatite related tendon, bursal and synovial inflammation; Behcet's disease; primary and secondary Sjogren's syndrome; systemic sclerosis and limited scleroderma; systemic lupus erythematosus, mixed connective tissue disease, and undifferentiated connective tissue disease; inflammatory myopathies including dermatomyositis and polymyositis; polymyalgia rheumatic; juvenile arthritis including idiopathic inflammatory arthritis of whatever joint distribution and associated syndromes, and rheumatic fever and its systemic complications; vasculitis including giant cell arteritis, Takayasu's arteritis, Churg-Strauss syndrome, polyarteritis nodos, microscopic polyarteritis, and vasculitis associated with viral infection, hypersensitivity reactions, cryoglobulins, and paraproteins; low back pain; Familial Mediterranean fever, Muckle-Wells syndrome, and Familial Hibernian Fever, Kikuchi disease; drug-induced arthralgias, tendonitis, and myopathies; and iii) A disease or condition concerning gastro-intestinal tract, preferably selected from the group consisting of eosinophilic gastro-enteritis, mastocytosis, Crohn's disease, colitis including ulcerative colitis, proctitis; coeliac disease, irritable bowel syndrome, and food-related allergies which may have effects remote from the gut, e.g. migraine, rhinitis or eczema in a patient suffering from, or at risk of, said disease or condition, which comprises administering to the patient an inventive pharmaceutical composition.

A sixth aspect of the present invention relates to the inventive pharmaceutical composition, the use of an inventive pharmaceutical composition and the inventive method of treating a patient, characterized in that the inventive pharmaceutical composition is sequentially or concurrently co-administered with one or more further pharmaceutical compositions, wherein the one or more active ingredients are preferably selected from the group consisting of non-steriodal anti-inflammatory agents; preferably non-selective cyclo-oxygenase COX-1/COX-2 inhibitors whether applied topically or systemically, e.g. piroxicam, diclofenac, propionic acids such as naproxen, flurbiprofen, fenoprofen, ketoprofen and ibuprofen, fenamates such as mefenamic acid, indomethacin, sulindac, ayapropayone, pyrayoleones such as phenylbutazone, salicylates such as aspirin, selective COX-2 inhibitors, e.g. meloxicam, celecoxib, rofecoxib, valdecoxib, lumarocoxib, parecoxib and etoricoxib, cyclo-oxygenase inhibiting nitric oxide donors (CINODs); glucocorticoid, preferably flunisolide, triamcinolone acetonide, betamethasone dipropionate, budesonide, fluticasone propionate, ciclesonide or mometasone furoate; methotrexate; leflunomide; hydroxychloroquine; d-penicillamine; diacerein; nutritional supplements, preferably glucosamine; gold preparations, preferably auranofin; cytokine or agonist or antagonist of cytokine function; monoclonal antibody targeting B-Lymphocytes, preferably CD20 (rituximab); MRA-alL16R; T-lymphocytes; CTLA4-Ig; HuMax 11-15; a modulator of chemokine receptor function, preferably an antagonist of CCR2, CCR2A, CCR2B, CCR3, CCR4, CCR5, CCR6, CCR7, CCR8, CCR9, CCRIO and CCRI I (for the C-C family), CXCRI, CXCR2, CXCR3, CXCR4 and CXCR5 (for the C-X-C family) and CX3CRI (for the C-X3-C family); azathioprine, tofacitinib, monoclonal antibodies, such as the anti tumour necrosis factor alpha monoclonal antibodies infliximab, adalimumab, and golimumab; interleukin 1 receptor antagonist, e.g. anakinra; etanercept, and abatacept; more preferably methotrexate and hydroxychloroquine.

The aspects of the present invention as set out hereinbefore can also comprise, if reasonable to a person skilled in the art, any possible combination of the preferred embodiments as set out in the dependent claims or disclosed in the following detailed description.

DETAILED DESCRIPTION OF THE INVENTION

Figure 1:
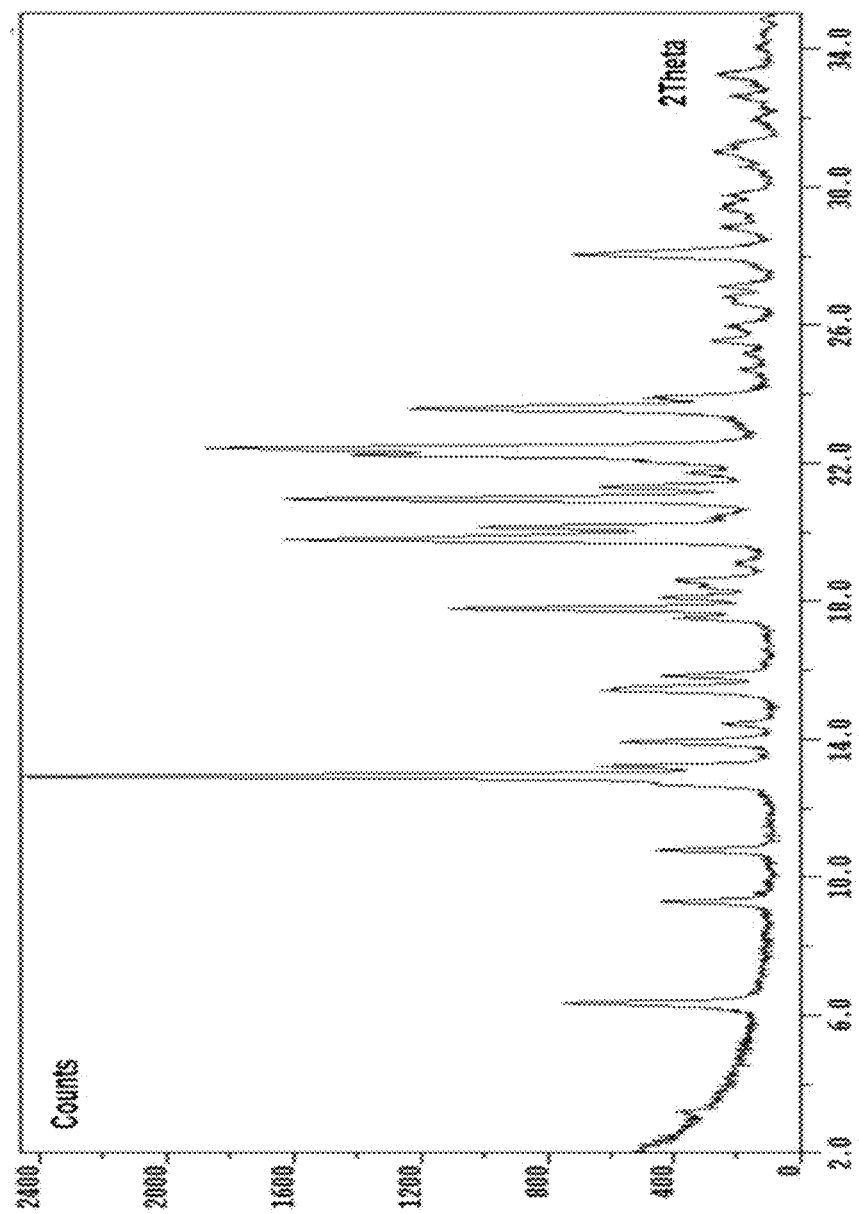
FIG. 1 represents an X-ray powder diffraction pattern of crystal Form A of the meglumine salt of sulfasalazine

The present inventors found out that while sulfasalazine free acid form is characterized as a low intestinal absorption compound (see Arik Dahan, Gordon L. Amidon; "Small intestinal efflux mediated by MRP2 and BCRP shifts sulfasalazine intestinal permeability from high to low, enabling its colonic targeting"; American Journal of Physiology—Gastrointestinal and Liver Physiology Published 21 Jul. 2009 Vol. 297 no. 2, G371-G377) having a low permeability through Caco-2 cell monolayers (Liang E, Chessic K, Yazdanian M.; "Evaluation of an accelerated Caco-2 cell permeability model."; J Pharm Sci. 2000 March; 89(3):336-45), the inventive pharmaceutical compositions of sulfasalazine instead display an improved permeability through Caco-2 cell monolayers as compared to free acid form of sulfasalazine (see Example 3, Table 3 below).

In addition, the free acid form of sulfasalazine is classified according to the United States Pharmacopoeia as practically insoluble (<0.1 mg/mL), having a solubility in de-ionized water at 24° C. of 0.031 mg/mL. According to measurements conducted by the present inventors the sulfasalazine free acid form exhibits a solubility of 0.06 mg/mL in de-ionized water at 24° C., while sulfasalazine applied as the inventive pharmaceutical composition exhibits an increased solubility in de-ionized water at 24° C. of generally ≥0.1 mg/mL, more preferably ≥0.5 mg/mL, ≥1 mg/mL (see example 1, Table 1 below).

Thus, due to the increased bioavailability and/or solubility a decreased dose of sulfasalazine may be used in therapeutic treatment of a disease or a condition in which modulation of inflammatory cells is beneficial that require systemic exposure to sulfasalazine, e.g. rheumatoid arthritis, ankylosing spondylitis and juvenile idiopathic arthritis, without altering the total systemic exposure to sulfasalazine. This leads to an improved risk-benefit profile due to a decreased exposure to sulfapyridine, the metabolite which is generally held responsible for some of the adverse events seen in patients treated with sulfasalazine (adverse events are exemplified in the background section of the present application). Particularly, slow-acetylating patients will benefit from the decreased exposure to sulfapyridine. Furthermore, compliance to the therapy may be improved due to the decreased burden of the therapy through the use of fewer and/or smaller solid pharmaceutical compositions (e.g. tablets, micro tablets, capsules, multiple unit pellet systems and the like).

Furthermore, the inventive process for preparing the inventive sulfasalazine pharmaceutical oral dosage composition is stable (see Example 2, Table 2 below). The term "stable" in the context of the present invention means that a measured value falls within range of specified values determined in accordance with a respective applicable regulatory guideline, e.g. the European Pharmacopeia.

The properties or the physical and chemical stability of the inventive pharmaceutical tablet composition may be tested in conventional manner, e.g. by measurement of appearance, hardness (or resistance to crushing), disintegration time, dissolution, friability, water content, assay for the inventive sulfasalazine salts and/or their degradation products (related substances), and/or uniformity of dosage units or mass after storage at controlled storage conditions; e.g. at intermediate and/or accelerated conditions according to ICH guideline Q1A(R2) (i.e. at 25° C./60% relative humidity (RH) and/or at 40° C./75% RH). These tests shall be performed according to applicable pharmaceutical regulatory standards as described e.g. in ICH or EMA guidelines and/or the European Pharmacopeia (EP).

At least some of these attributes, i.e. properties or physical and chemical stability, preferably most of these attributes and most preferably all of these attributes of the inventive pharmaceutical tablet composition are stable over time and different controlled storage conditions. According to a preferred embodiment the dissolution (profile) of the inventive pharmaceutical tablet composition according to the present invention, e.g. a tablet or film-coated tablet, is stable over at least 6 months when stored preferably in Alu-Alu blisters at intermediate or long-term storage conditions, i.e. 25° C./60% RH or 40° C./75% RH. More preferably, dissolution and further additional attributes such as, e.g., assay, related substances or uniformity of dosage units or mass are also stable after storage over at least 6 months when stored at intermediate or long-term storage conditions.

According to a first aspect of the present invention, the inventive process for preparing the pharmaceutical composition for oral administration comprising 2-hydroxy-5-[2-[4-[(2-pyridinylamino)sulfonyl]phenyl]diazenyl]-benzoic acid (sulfasalazine) as free acid form and/or sulfasalazine organic salt is provided.

According to step A) of the inventive preparation process for obtaining the inventive pharmaceutical composition, a suitable amount of sulfasalazine is provided. According to all aspects of the present invention sulfasalazine can be provided as free acid form. Alternatively or cumulatively, sulfasalazine may also be provided in salt form, preferably organic salt form, e.g. organic amine salt form, preferably as crystal Form A of the D(−)-N-methylglucamine (meglumine) salt of sulfasalazine, crystal Form A of the piperazine salt of sulfasalazine, crystal Form A of the diethylamine salt of sulfasalazine and crystal Form B of the diethylamine salt of sulfasalazine. The suitable amount of sulfasalazine is preferably chosen so that the prepared inventive pharmaceutical composition comprises—depending on the mode of administration—from 0.01 to 100 wt.-%, from 1 to 90 wt.-%, from 25 to wt.-%, from 30 to 70 wt.-%, from 40 to 60 wt.-%, or 50 wt.-% of sulfasalazine respectively based on the total weight of the inventive pharmaceutical composition.

According to the present invention, the phrase "crystal Form A of the D(−)-N-methylglucamine salt of sulfasalazine" may be used synonymously to "crystal Form A of the meglumine salt of sulfasalazine", "Form A meglumine salt", "Form A meglumine sulfasalazine" or "meglumine sulfasalazine salt".

According to the present invention, the phrase "crystal Form A of the piperazine salt of sulfasalazine" may be used synonymously to "crystal Form A of the piperazine salt of sulfasalazine", "Form A piperazine salt", "Form A piperazine sulfasalazine" or "piperazine sulfasalazine salt".

According to the present invention, the phrase "crystal Form A of the diethylamine salt of sulfasalazine" may be used synonymously to "crystal Form A of the diethylamine salt of sulfasalazine", "Form A diethylamine salt", or "Form A diethylamine sulfasalazine". According to an optional alternative embodiment of the present invention, crystal Form A of the diethylamine salt of sulfasalazine is not comprised in all aspects of the present invention, in particular the inventive pharmaceutical composition.

According to the present invention, the phrase "crystal Form B of the diethylamine salt of sulfasalazine" may be used synonymously to "crystal Form B of the diethylamine salt of sulfasalazine", "Form B diethylamine salt", or "Form B diethylamine sulfasalazine". According to an optional alternative embodiment of the present invention, crystal Form B of the diethylamine salt of sulfasalazine is not comprised in all aspects of the present invention, in particular the inventive pharmaceutical composition.

According to a further optional alternative embodiment of the present invention, the inventive pharmaceutical composition does not comprise a diethylamine salt of sulfasalazine.

According to an embodiment of all aspects of the present invention, the crystal salts of sulfasalazine are preferably at least 50 wt.-%, 60 wt.-%, 70 wt.-%, 80 wt.-%, 90 wt.-%, 95 wt.-%, 96 wt.-%, 97 wt. %, 98 wt.-%, 99% or 100 wt.-% crystalline based on the total weight of the respective salt form of sulfasalazine. Crystallinity can be estimated by conventional X-ray diffractometric techniques.

According to a further embodiment concerning all aspects of the present invention, crystal Form A of the meglumine salt of sulfasalazine exhibits at least the following characteristic X-ray powder diffraction (XRPD) peaks (expressed in degrees 2θ±0.2 degrees) (the margin of error being consistent with the United States Pharmacopeia general chapter on X-ray diffraction (USP941)—see the United States Pharmacopeia Convention. X-Ray Diffraction, General Test <941>. *United States Pharmacopeia*, 25th ed. Rockville, MD: United States Pharmacopeial Convention; 2002: 2088-2089):

(1) 6.35, 13.93 and 22.41, or
(2) 9.31, 15.86 and 20.99, or
(3) 6.35, 13.93, 15.48, 15.86, 22.41 and 23.60, or
(4) 6.35, 10.79, 12.93, 13.93, 15.48, 15.86, 18.12, 19.82 and 22.41, or
(5) 9.31, 10.79, 12.93, 13.93, 14.47, 15.48, 15.86, 17.56, 19.10, 23.60 and 28.07, or
(6) 6.35, 12.93, 13.93, 14.47, 15.48, 15.86, 19.10, 19.82, 20.99, 21.27, 22.41, 23.60, 23.89 and 28.07, or
(7) 6.35, 9.31, 10.79, 12.93, 13.93, 14.47, 15.48, 15.86, 17.78, 18.12, 19.82, 20.11, 20.99, 21.27, 22.41, 23.60, 23.89, 28.07 and 28.80, or
(8) 6.35, 9.31, 10.79, 12.93, 13.93, 14.47, 15.48, 15.86, 17.56, 17.78, 18.12, 18.50, 19.10, 19.82, 20.99, 21.27, 22.41, 23.60, 23.89, 24.70, 25.14, 25.55, 25.93, 26.81, 28.07 and 28.80, or
(9) 6.35, 9.31, 10.79, 12.93, 13.93, 14.47, 15.48, 15.86, 17.56, 17.78, 18.12, 18.50, 19.10, 19.82, 20.11, 20.99, 21.27, 22.41, 23.60, 23.89, 24.70, 25.14, 25.55, 25.93, 26.81, 28.07, 28.80, 29.49, 32.01, 32.58, 33.23.

According to a preferred embodiment concerning all aspects of the present invention, Form A meglumine salt exhibits at least the following characteristic XRPD peaks: 6.35, 13.93, 15.48, 15.86, 22.41, 23.60 and 28.07.

In FIG. 1, a characteristic XRPD spectrum of crystal Form A of meglumine salt of sulfasalazine is provided.

According to another alternative of cumulative embodiment concerning all aspects of the present invention crystal Form A of the piperazine salt of sulfasalazine exhibits at least the following characteristic X-ray powder diffraction (XRPD) peaks (expressed in degrees 2θ±0.2 degrees) (the margin of error being consistent with the United States Pharmacopeia general chapter on X-ray diffraction (USP941)—see the United States Pharmacopeia Convention. X-Ray Diffraction, General Test <941>. *United States Pharmacopeia*, 25$^{th}$ ed. Rockville, MD: United States Pharmacopeial Convention; 2002: 2088-2089):

(1) 11.95, 12.30 and 16.42, or
(2) 12.30, 12.93 and 15.01, or
(3) 11.95, 12.30, 12.93, 16.42, 17.87 and 20.36, or
(4) 8.11, 11.95, 12.30, 15.01, 16.42, 17.87, 20.36 and 20.74, or
(5) 11.95, 12.30, 12.93, 15.01, 16.42, 17.87, 20.36, 20.74, 22.41 and 23.41 or
(6) 11.95, 15.01, 16.42, 17.87, 20.36, 20.74, 23.41, 24.01, 24.67, 24.99 and 26.09, or
(7) 8.11, 11.95, 12.30, 12.93, 15.01, 16.42, 17.87, 20.36, 20.74, 22.41, 23.41, 24.01, 24.67, 24.99 and 26.09, or
(8) 11.95, 12.30, 12.93, 15.01, 16.42, 17.87, 20.36, 20.74, 22.41, 23.41, 24.01, 24.67, 24.99, 26.09, 26.81, 27.73 and 28.80, or
(9) 8.11, 11.95, 12.30, 12.93, 15.01, 16.42, 17.87, 20.36, 20.74, 22.41, 23.41, 24.01, 24.67, 24.99, 26.09, 26.81, 27.73, 28.80, 29.80 and 30.43.

According to a preferred embodiment concerning all aspects of the present invention, the Form A piperazine salt exhibits at least the following characteristic XRPD peaks: 12.3, 12.93, 15.0, 16.42, 22.41 and 23.41.

Figure 2:
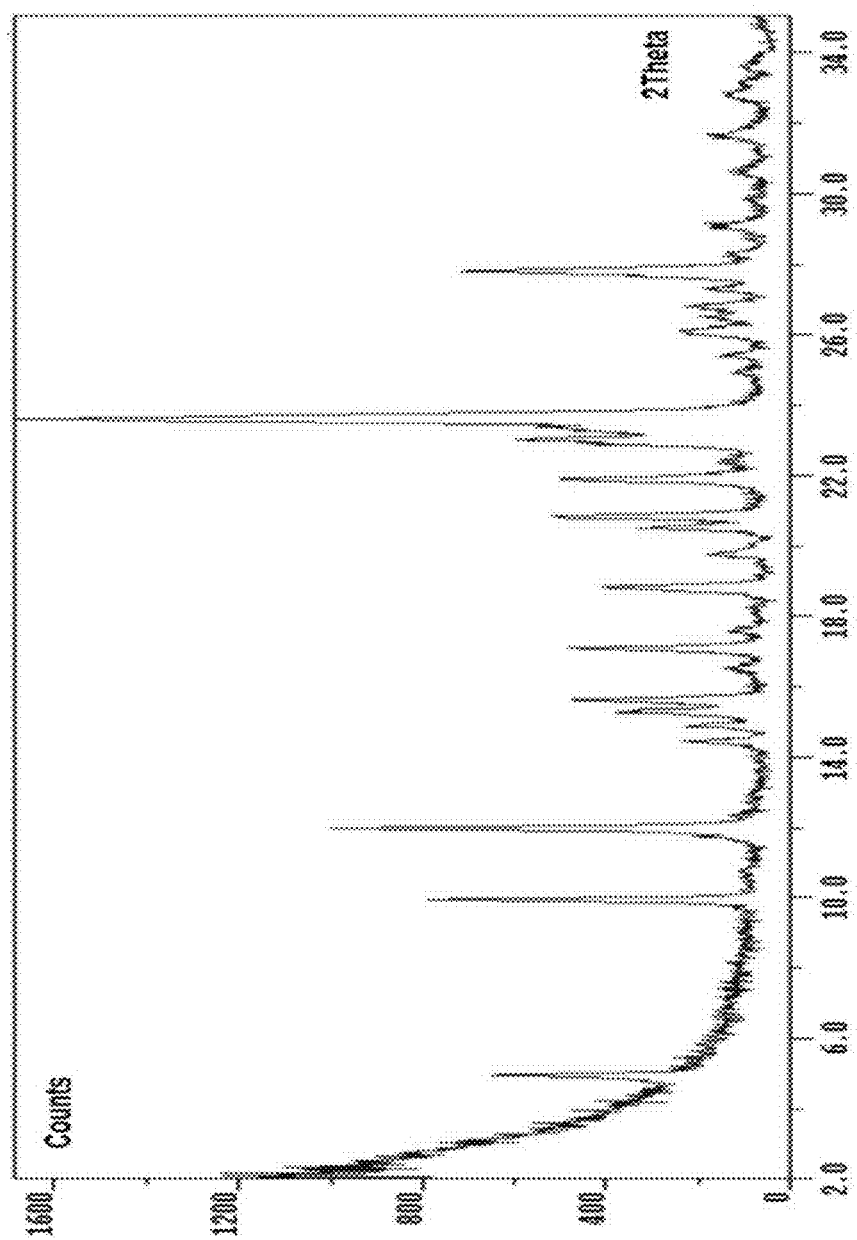
FIG. 2 represents an X-ray powder diffraction pattern of crystal Form A of the piperazine salt of sulfasalazine

In FIG. 2, a characteristic XRPD spectrum of inventive crystal Form A of piperazine salt of sulfasalazine is provided.

According to another alternative or cumulative embodiment concerning all aspects of the present invention the inventive crystal Form A of the diethylamine salt of sulfasalazine exhibits at least the following characteristic X-ray powder diffraction (XRPD) peaks (expressed in degrees 2θ±0.2 degrees) (the margin of error being consistent with the United States Pharmacopeia general chapter on X-ray diffraction (USP941)—see the United States Pharmacopeia Convention. X-Ray Diffraction, General Test <941>. *United States Pharmacopeia*, 25$^{th}$ ed. Rockville, MD: United States Pharmacopeial Convention; 2002: 2088-2089):

(1) 7.16, 11.48, and 18.78, or
(2) 10.50, 15.41 and 21.87, or
(3) 7.16, 10.50, 11.48, 18.78, 21.65 and 21.87, or
(4) 10.50, 11.48, 12.42, 14.38, 15.41, 16.64, 18.78 and 21.87, or
(5) 7.16, 10.50, 11.01, 11.48, 13.87, 15.92, 16.64, 18.78, 21.08, 21.65 and 22.15, or
(6) 7.16, 10.50, 11.01, 11.48, 12.42, 13.87, 14.38, 15.41, 15.92, 16.64, 17.19, 18.28, 18.78, 21.08, 21.65, 21.87, and 22.15 or
(7) 7.16, 10.50, 11.48, 12.42, 13.87, 14.38, 15.41, 15.92, 16.64, 20.52, 21.08, 21.65, 21.87, 22.15, 22.47, 23.16, 23.63, 24.14 and 25.11, or
(8) 7.16, 10.50, 11.01, 11.48, 12.42, 13.87, 14.38, 15.41, 15.92, 16.64, 17.19, 18.28, 18.78, 20.52, 21.08, 21.65, 21.87, 22.15, 22.47, 23.16, 23.63, 24.14 and 25.11, or
(9) 7.16, 10.50, 11.01, 11.48, 12.42, 13.87, 14.38, 15.41, 15.92, 16.64, 17.19, 18.28, 18.78, 20.52, 21.08, 21.65, 21.87, 22.15, 22.47, 23.16, 23.63, 24.14, 25.11, 26.94, 27.95, 28.92, 29.46.

According to a preferred embodiment concerning all aspects of the present invention, the Form A diethylamine salt exhibits at least the following characteristic XRPD peaks: 7.16, 10.50, 11.48, 18.78, 21.65 and 21.87.

Figure 3:
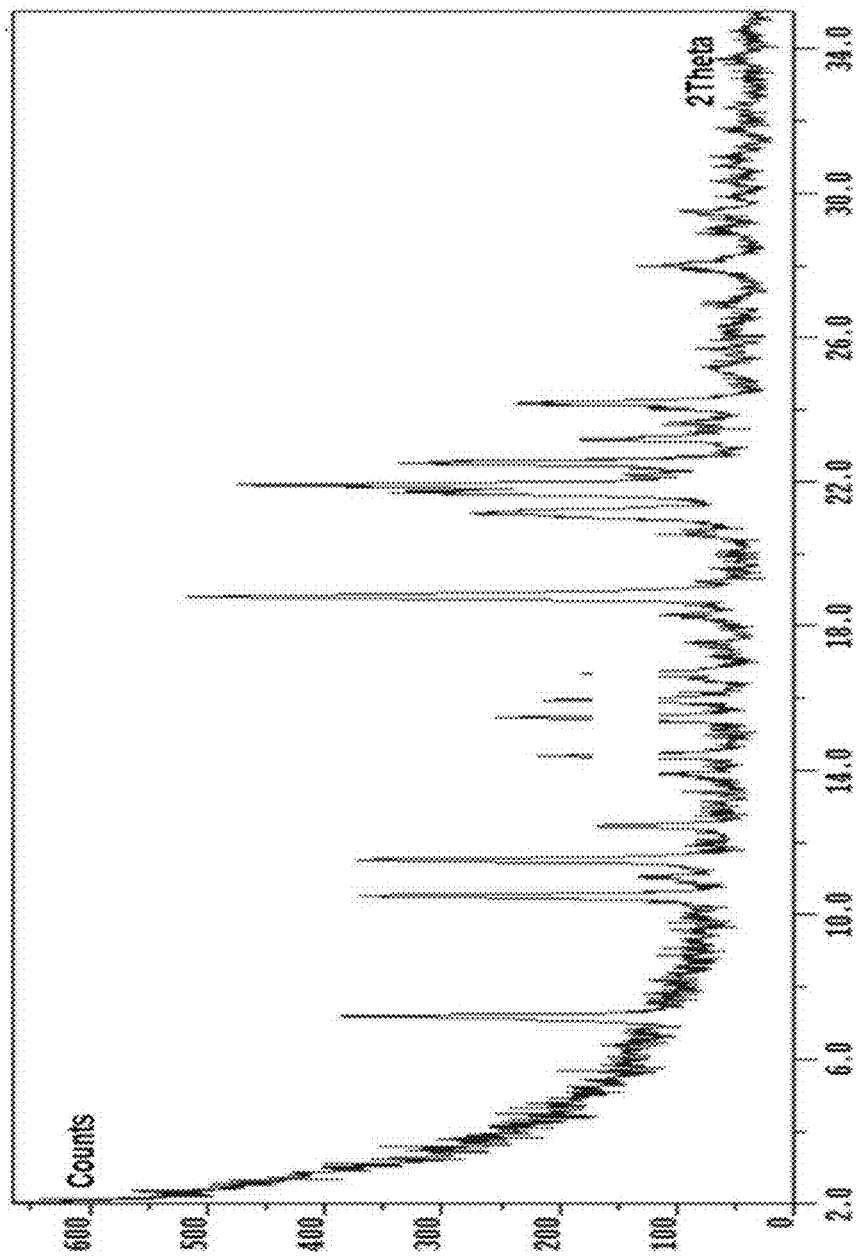
FIG. 3 represents an X-ray powder diffraction pattern of crystal Form A of the diethylamine salt of sulfasalazine

In FIG. 3, a characteristic XRPD spectrum of inventive crystal Form A of diethylamine salt of sulfasalazine is provided.

According to an another alternative or cumulative embodiment concerning all aspects of the present invention a second polymorph crystal Form B of the diethylamine salt of sulfasalazine exhibits at least the following characteristic X-ray powder diffraction (XRPD) peaks (expressed in degrees 2θ±0.2 degrees) (the margin of error being consistent with the United States Pharmacopeia general chapter on X-ray diffraction (USP941)—see the United States Pharmacopeia Convention. X-Ray Diffraction, General Test <941>. *United States Pharmacopeia*, 25$^{th}$ ed. Rockville, MD: United States Pharmacopeial Convention; 2002: 2088-2089):

(1) 6.85, 17.82 and 22.75, or
(2) 11.38, 20.58 and 23.98, or
(3) 6.85, 11.38, 17.62, 20.58 and 22.75, or
(4) 6.85, 11.38, 11.70, 17.62, 20.58, 22.75 and 23.98, or
(5) 11.38, 11.70, 15.29, 16.71, 17.62, 19.92, 20.58, 21.30, 22.75, 23.63 and 23.98, or
(6) 6.85, 11.38, 11.70, 14.78, 15.29, 15.70, 16.71, 17.62, 19.92, 20.20, 20.58, 21.30, 22.75, 23.63, 23.98 and 28.61 or
(7) 6.85, 11.38, 11.70, 14.78, 15.29, 15.70, 16.71, 17.62, 19.92, 20.20, 20.58, 21.30, 22.75, 23.63, 23.98, 25.05, 25.71, 26.81, 27.95 and 28.61, or
(8) 6.85, 11.38, 11.70, 14.78, 15.29, 15.70, 16.71, 17.62, 19.92, 20.20, 20.58, 21.30, 22.75, 23.63, 23.98, 25.05, 25.71, 26.81, 27.51, 27.95, 28.61, 29.14, 31.06.

According to a preferred embodiment concerning all aspects of the present invention, the Form B diethylamine salt exhibits at least the following characteristic XRPD peaks: 6.85, 11.38, 11.70, 17.62, 20.58, 22.75 and 23.98.

Figure 4:
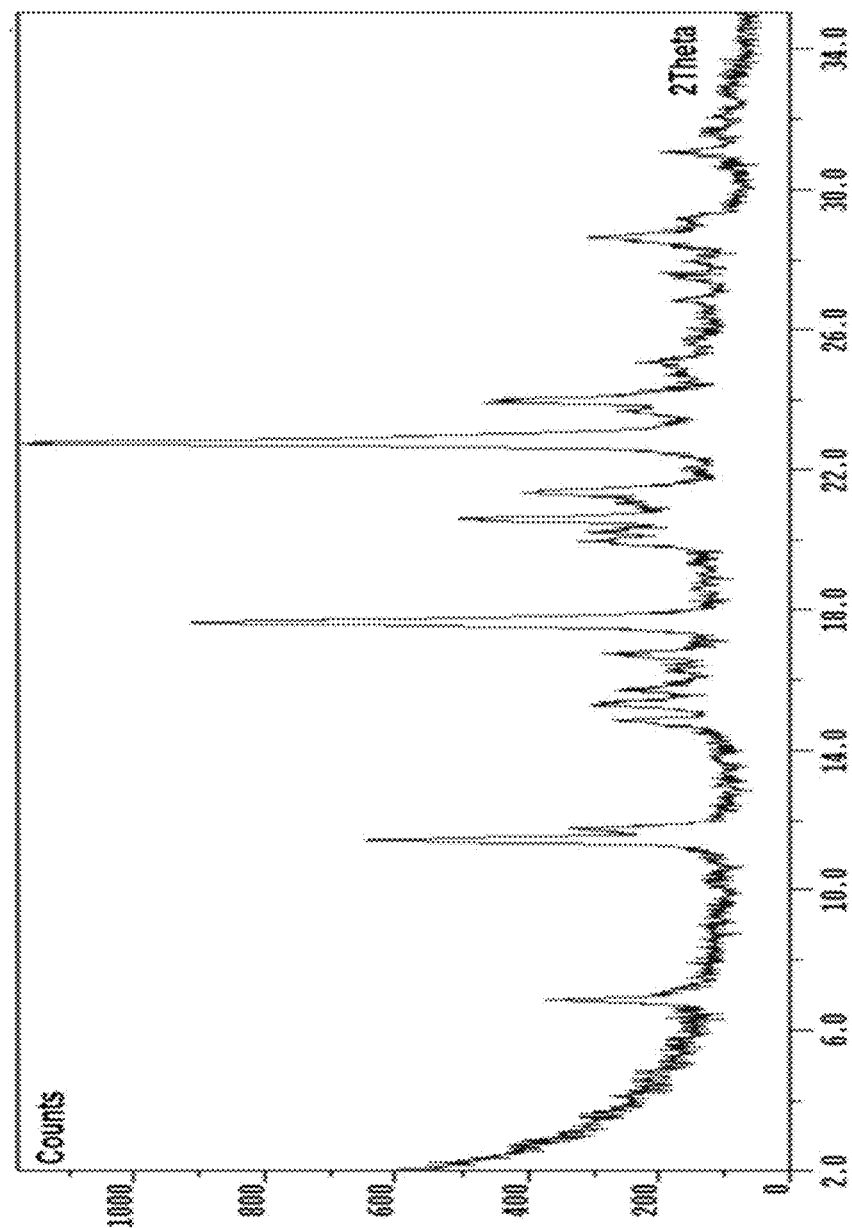
FIG. 4 represents an X-ray powder diffraction pattern of crystal Form B of the diethylamine salt of sulfasalazine

In FIG. 4, a characteristic XRPD spectrum of inventive crystal Form B of diethylamine salt of sulfasalazine is provided.

Although the crystal salt forms of sulfasalazine, namely crystal Form A of the D(−)-N-methylglucamine (meglumine) salt of sulfasalazine, crystal Form A of the piperazine salt of sulfasalazine, crystal Form A of the diethylamine salt of sulfasalazine and crystal Form B of the diethylamine salt of sulfasalazine, are preferably used in solvate and/or hydrate free from. Such a solvate-free, in particular hydrate-free (anhydrous) form may exhibit advantageous physico-chemical properties when manufacturing the pharmaceutical composition, as the solvate-free, in particular the anhydrous form supports in particular the physical and chemical stability of the active ingredient sulfasalazine and the pharmaceutical composition respectively over shelf life.

The crystalline organic salts of 2-hydroxy-5-[2-[4-[(2-pyridinylamino)sulfonyl]phenyl]diazenyl]-benzoic acid (sulfasalazine), wherein the organic salts are preferably selected from diethylamine, piperazine and D-(−)-N-methylglucamine (meglumine), are preferably prepared according to the process comprising or consisting of the following steps:

A1. Providing sulfasalazine free acid form in a suitable solvent,

B1: Providing an organic amine containing constituent, preferably selected from meglumine, piperazine and diethylamine, in a suitable solvent, C1: Mixing the sulfasalazine solution of step A1) with the organic amine containing constituent solution of step B1) at room temperature, preferably 19° C. to 25° C., and D1: Separating the crystals of Form A diethylamine sulfasalazine or solvates thereof or the crystals of Form A piperazine sulfasalazine or solvates thereof or the crystals of Form A meglumine sulfasalazine or solvates thereof formed in the solution of step C1), or A2: Providing sulfasalazine free acid form in a suitable solvent, B2: Providing an organic amine containing constituent, preferably selected from meglumine and diethylamine, in a suitable solvent, C2: Mixing the sulfasalazine solution of step A2) with the organic amine containing constituent solution of step B2), wherein the amine containing constituent has a molar excess with respect to sulfasalazine of at least 5%, more preferably at least 10%, more preferably at least 20%, and D2a: Concentrating the mixed solution formed in step C2) and separating the crystals of Form A meglumine sulfasalazine or solvates thereof of the crystals of Form B diethylamine sulfasalazine or solvates thereof or D2b: Adding a further solvent to the mixed solution formed in step C2, wherein the further solvent is different from the solvents used in step A2 and B2 and separating the crystals of Form A meglumine sulfasalazine or solvates thereof of the crystals of Form B diethylamine sulfasalazine or solvates thereof, wherein the organic amine containing constituent does not represent Tris(hydroxymethyl)aminomethane (Tromethane Base).

In case the crystal salt forms of sulfasalazine comprise residue solvate/hydrate a suitable drying step is conducted subsequently.

According to step B) of the inventive preparation process for obtaining the inventive pharmaceutical composition, an organic amine containing constituent suitable for pharmaceutical use, preferably selected from meglumine, piperazine and diethylamine, is provided, wherein the organic amine containing constituent does not represent Tris(hydroxymethyl)aminomethane (Tromethane Base). The organic amine containing constituent is preferably provided in powder form.

According to step C) of the inventive preparation process for obtaining the inventive pharmaceutical composition, one or more pharmaceutical excipients and optionally one or more further active ingredients are further provided.

According to all aspects of the present invention, the one or more pharmaceutical excipients provided in step C) are preferably selected from the group of filler agents, binder agents, lubricant agents, disintegrant agents, surfactant/solubilizing agents, alkaline additives, antacid agents; pH buffering agents; colorant agents; pigment agents; flavouring agents; thickening agents; plasticizer agents; solvent agents; anti-tacking agents; anti-static agents; anti-foaming agents; dispersant agents; other polymer agents; and hard and soft gelatin capsule forming agents.

Alternatively or cumulatively the one or more further active ingredients of step C) are preferably selected from the group consisting of methotrexate, hydroxychloroquine, steroids, leflunomide, azathioprine, tofacitinib, monoclonal antibodies, such as the anti tumour necrosis factor alpha monoclonal antibodies infliximab, adalimumab, and golimumab, more preferably methotrexate and hydroxychloroquine, preferably selected from the group consisting of non-steriodal anti-inflammatory agents; preferably non-selective cyclo-oxygenase COX-1/COX-2 inhibitors whether applied topically or systemically, e.g. piroxicam, diclofenac, propionic acids such as naproxen, flurbiprofen, fenoprofen, ketoprofen and ibuprofen, fenamates such as mefenamic acid, indomethacin, sulindac, ayapropayone, pyrayoleones such as phenylbutazone, salicylates such as aspirin, selective COX-2 inhibitors, e.g. meloxicam, celecoxib, rofecoxib, valdecoxib, lumaracoxib, parecoxib and etoricoxib, cyclo-oxygenase inhibiting nitric oxide donors (CINODs); glucocorticoid, preferably flunisolide, triamcinolone acetonide, betamethasone dipropionate, budesonide, fluticasone propionate, ciclesonide or mometasone furoate; methotrexate; leflunomide; hydroxychloroquine; d-penicillamine; diacerein; nutritional supplements, preferably glucosamine; gold preparations, preferably auranofin; cytokine or agonist or antagonist of cytokine function; monoclonal antibody targeting B-Lymphocytes, preferably CD20 (rituximab); MRA-alL16R; T-lymphocytes; CTLA4-Ig; HuMax 11-15; a modulator of chemokine receptor function, preferably an antagonist of CCR2, CCR2A, CCR2B, CCR3, CCR4, CCR5, CCR6, CCR7, CCR8, CCR9, CCRIO and CCRI I (for the C-C family), CXCRI, CXCR2, CXCR3, CXCR4 and CXCR5 (for the C-X-C family) and CX3CRI (for the C-X3-C family); azathioprine, tofacitinib, monoclonal antibodies, such as the anti tumour necrosis factor alpha monoclonal antibodies infliximab, adalimumab, and golimumab; interleukin 1 receptor antagonist, e.g. anakinra; etanercept, and abatacept; more preferably methotrexate and hydroxychloroquine.

According to step D) of the inventive preparation process for obtaining the inventive pharmaceutical composition, a therapeutically effective amount of sulfasalazine of step A) with a suitable amount of the organic amine containing constituent of step B) and the one or more pharmaceutical excipients and optionally one or more further active ingredient of step C) are mixed to form the pharmaceutical composition for oral administration.

According to an alternatively or cumulatively preferred embodiment of all aspects of the present invention, a core material comprising sulfasalazine and/or an organic sulfasalazine amine salt is formed in step D), wherein the core material is preferably prepared by D1: a method selected from the group consisting of wet extrusion, wet spheronization, hot melt extrusion, hot melt pelletization, fluidized bed spray encapsulation, balling and compression.

More preferably to an alternatively or cumulatively preferred embodiment of all aspects of the present invention, the one or more pharmaceutical excipients in step C) comprise or consist of a seed material as filler, in particular a water insoluble seed material, preferably selected from the group consisting of oxide materials, cellulose materials, organic polymer materials or mixtures thereof, and/or a water soluble seed material, preferably selected from the group consisting of inorganic salt materials, sugar materials, starch martials or mixtures thereof, such as nonpareils, and wherein in step D) the core material is prepared by D2: coating the seed material provided in step C) with sulfasalazine provided in step A) and the organic amine constituent provided in step B) and optionally using further pharmaceutical excipients provided in step C) preferably selected from the group consisting of binder agents, surfactant agents, filler agents, lubricant agents, disintegrating agents, alkaline additives and buffering agents.

According to an alternatively or cumulatively preferred embodiment of all aspects of the present invention, the inventive preparation process further comprises or consists of applying one or more coating layers to the core material provided in D) to form the pharmaceutical composition for oral administration, the process further comprising or consisting of the following steps:

E: optionally coating the core material prepared in step D) with one or more separating layers, preferably selected from pH buffering agents, F: coating the core material prepared in step D) or the core material comprising one or more separating layers prepared in step E) with an enteric coating and G: optionally coating the enteric coated core material of step F) with an over-coating layer, and H: optionally formulating the enteric coated core material of step F) or the over-coated enteric coated core material of step G) into a tablet or a capsule.

According to an alternative or cumulative preferred embodiment of all aspects of the present invention, the coating in any one of steps E) through H) is preferably prepared by powder or solution layering, more preferably by spray drying or spray congealing.

According to an alternative or cumulative preferred embodiment of all aspects of the present invention, the core material of step D) or the core material comprising one or more separating layers of step E) is compressed to form a tablet prior to coating the compressed core material with the enteric coating in step F).

According to an alternatively or cumulatively preferred embodiment of all aspects of the present invention, one or more pharmaceutical excipients suitable to form the one or more separating layers of step E) are preferably selected from the group consisting of film forming agents, preferably sugar, polyethylene glycol, polyvinylpyrrolidone, polyvinyl alcohol, polyvinyl acetate, hydroxypropyl cellulose, methylcellulose, ethylcellulose, hydroxypropyl methylcellulose, and carboxymethylcellulose sodium; antacid agents, preferably magnesium oxide, hydroxide or carbonate, aluminum or calcium hydroxide, carbonate or silicate; composite aluminum/magnesium compounds, e.g. $Al_2O_3 \cdot 6\ MgO \cdot CO_2 \cdot 12\ H_2O$, $Mg_6Al_2(OH)_{16}CO_3 \cdot 4\ H_2O$, $MgO \cdot Al_2O_3 \cdot 2\ SiO_2 \cdot n\ H_2O$, aluminium hydroxide/sodium bicarbonate co-precipitate; and pharmaceutically acceptable pH-buffering agents, e.g. sodium, potassium, calcium, magnesium and aluminum salts of phosphoric, carbonic, citric or other suitable, weak, inorganic or organic acids; or suitable organic bases, e.g. basic amino acids and salts thereof; plasticizer agents; colorant agents; pigment agents; filler agents; and anti-tacking agents/anti-static agents, preferably magnesium stearate, titanium dioxide, and talc.

According to an alternatively or cumulatively preferred embodiment of all aspects of the present invention, one or more pharmaceutical excipients suitable to form the enteric coating of step F) are preferably selected from the group consisting of film forming agents, preferably methacrylic acid copolymers, cellulose acetate phthalate, hydroxypropyl methylcellulose phthalate, hydroxypropyl methylcellulose acetate succinate, polyvinyl acetate phthalate, cellulose acetate trimellitate, carboxymethylethylcellulose, and shellac; plasticizer agents, preferably triacetin, citric acid esters, phthalic acid esters, dibutyl sebacate, cetyl alcohol, polyethylene glycols, and polysorbates; dispersant agents; colorant agents; pigment agents; other polymer agents, e.g. poly(ethylacrylat, methylmethacrylat); anti-tacking/anti-foaming agents, pharmaceutical agents to increase film thickness and/or to decrease diffusion of acidic gastric juices into the core material. More preferably according to all aspects of the present invention, the enteric coating layer has a thickness of at least 5 µm, more preferably at least 10 µm.

According to an alternatively or cumulatively preferred embodiment of all aspects of the present invention, one or more pharmaceutical excipients suitable to form the over-coating of step G) are selected from the group consisting of film forming agents, preferably sugar, polyethylene glycol, polyvinylpyrrolidone, polyvinyl alcohol, polyvinyl acetate, hydroxypropyl cellulose, methylcellulose, ethylcellulose, hydroxypropyl methyl cellulose, and carboxymethylcellulose sodium; plasticizer agents; colorant agents; pigment agents; filler agents; anti-tacking agents; anti-static agents, preferably magnesium stearate, titanium dioxide, and talc.

According to an alternatively or cumulatively preferred embodiment of all aspects of the present invention, the capsule in step H) is formed
i. as a soft gelatin capsule, preferably using one or more further pharmaceutical excipients selected from the group consisting of surfactant/solubilizing agents, preferably Tocopheryl Polyethylene Glycol Succinate (TPGS); vegetable oil and/or polyethylene glycol.
ii. as a hard gelatin capsule, one or more further pharmaceutical excipients selected from the group consisting of surfactant/solubilizing agents, preferably Tocopheryl Polyethylene Glycol Succinate (TPGS).

According to the second aspect, the present invention relates to a pharmaceutical composition for oral administration obtainable according to an inventive preparation process.

According to an alternatively or cumulatively preferred embodiment of all aspects of the present invention, the inventive pharmaceutical composition for oral administration is a solid pharmaceutical composition, preferably selected from the group consisting of granules, preferably multiple unit pellets system (MUPS), tablets, preferably multiple unit pellet tablets (MUP tablets), capsules, and powders; or a liquid pharmaceutical composition, preferably selected from the group consisting of syrups and suspensions.

According to an alternative embodiment of the inventive pharmaceutical composition for oral administration, the inventive composition is alternatively or cumulatively suitable for dispersion in an aqueous liquid with neutral or slightly acidic pH-value before being orally administered or fed through a naso-gastric tube.

In case the inventive pharmaceutical composition may alternatively be in the form of a tablet formulation, the one, two, three, four or more pharmaceutical tablet excipients are preferably selected from the group consisting of filler agents, binder agents, disintegrant agents, lubricant agents and the like and compressed into tablets.

In case the inventive pharmaceutical composition may alternatively be in the form of liquid preparations for oral administration, e.g. in the form of syrups or suspensions, the pharmaceutical excipients comprised in such liquid preparations may comprise sugar and/or a mixture of ethanol, water, glycerol and propylene glycol, preferably buffered to a suitable pH. Optionally such inventive liquid preparation may contain one, two, three, four or more further excipients, preferably selected from the group consisting of colouring agents, flavouring agents, saccharine and/or carboxmethylcellulose as a thickening agent or other excipients known to those skilled in the art.

According to a further alternatively or cumulatively preferred embodiment of all aspects of the present invention, the total therapeutically effective amount of sulfasalazine as free acid or as organic salt per dose of the pharmaceutical composition for oral administration ranges from 10 mg to 2,000 mg, preferably 10 mg, 20 mg, 25 mg, 30 mg, 40 mg, 50 mg, 60 mg, 70 mg, 75 mg, 80 mg, 90 mg, 100 mg, 110 mg, 120 mg, 125 mg, 130 mg, 140 mg, 150 mg, 160 mg, 170 mg, 175 mg, 180 mg, 190 mg, 200 mg, 210 mg, 220 mg, 225 mg, 230 mg, 240 mg, 250 mg, 260 mg, 270 mg, 275 mg, 280 mg, 290 mg, 300 mg, 310 mg, 320 mg, 325 mg, 330 mg, 340 mg, 350 mg, 360 mg, 370 mg, 375 mg, 380 mg, 390 mg, 400 mg, 410 mg, 420 mg, 425 mg, 430 mg, 440 mg, 450 mg, 460 mg, 470 mg, 475 mg, 480 mg, 490 mg, 500 mg, 525 mg, 550 mg, 575 mg, 600 mg, 625 mg, 650 mg, 675 mg, 700 mg, 725 mg, 750 mg, 775 mg, 800 mg, 825 mg, 850 mg, 875 mg, 900 mg, 925 mg, 950 mg, 975 mg, 1,000 mg, 1,025 mg, 1,050 mg, 1,075 mg, 1,100 mg, 1,125 mg, 1,150 mg, 1,175 mg, 1,200 mg, 1,225 mg, 1,250 mg, 1,275 mg, 1,300 mg, 1,325 mg, 1,350 mg, 1,375 mg, 1,400 mg, 1,425 mg, 1,450 mg, 1,475 mg, 1,500 mg, 1,525 mg, 1,550 mg, 1,575 mg, 1,600 mg, 1,625 mg, 1,650 mg, 1,675 mg, 1,700 mg, 1,725 mg, 1,750 mg, 1,775 mg, 1,800 mg, 1,825 mg, 1,850 mg, 1,875 mg, 1,900 mg, 1,925 mg, 1,950 mg, 1,975 mg, 2,000 mg. More preferably, the single unit dosage of the inventive pharmaceutical composition comprises preferably <500 mg, ≤450 mg, ≤400 mg, ≤375 mg, ≤250 mg of sulfasalazine as free acid and/or as organic amine salt.

The inventive crystal salt forms of sulfasalazine and their in vivo metabolites sulfapyridine and 5-ASA are useful as modulators of function of various inflammatory cell types such as T cells, B cells, dendritic cells, neutrophils, NK cells and mast cells. For example, in experiments that studied the proliferation of human synovial cells of patients with rheumatoid arthritis, it was shown that the proliferation of these cells as well as the production of IL-1B and IL-6 by these cells were significantly inhibited. In these experiments it could be shown, that the overexpression of c-fos mRNA was inhibited by the inventive crystal forms of sulfasalazine. Thus, the inventive crystal forms of sulfasalazine may be administered to a mammal, including man, in particular for the treatment of autoimmune, inflammatory, proliferative and hyperproliferative diseases and immunologically-mediated diseases.

Thus, according to the third aspect, the present invention the inventive pharmaceutical composition is used in the treatment of
i) A human disease or condition in which modulation of inflammatory cells is beneficial,
ii) A disease or condition concerning bones or joints, preferably selected from the group consisting of arthritis associated with or including osteoarthritis/osteoarthrosis, both primary and secondary to, for example, congenital hip dysplasia; cervical and lumbar spondylitis, and low back and neck pain; rheumatoid arthritis and Still's disease; seronegative spondyloarthropathies including ankylosing spondylitis, psoriatic arthritis, reactive arthritis and undifferentiated spondarthropathy, septic arthritis and other infection-related arthopathies and bone disorders such as tuberculosis, including Potts' disease and Poncet's syndrome; acute and chronic crystal-induced synovitis including urate gout, calcium pyrophosphate deposition disease, and calcium apatite related tendon, bursal and synovial inflammation; Behcet's disease; primary and secondary Sjogren's syndrome; systemic sclerosis and limited scleroderma; systemic lupus erythematosus, mixed connective tissue disease, and undifferentiated connective tissue disease; inflammatory myopathies including dermatomyositis and polymyositis; polymyalgia rheumatic; juvenile arthritis including idiopathic inflammatory arthritis of whatever joint distribution and associated syndromes, and rheumatic fever and its systemic complications; vasculitis including giant cell arteritis, Takayasu's arteritis, Churg-Strauss syndrome, polyarteritis nodos, microscopic polyarteritis, and vasculitis associated with viral infection, hypersensitivity reactions, cryoglobulins, and paraproteins; low back pain; Familial Mediterranean fever, Muckle-Wells syndrome, and Familial Hibernian Fever, Kikuchi disease; drug-induced arthralgias, tendonitis, and myopathies; and
iii) A disease or condition concerning gastro-intestinal tract, preferably selected from the group consisting of eosinophilic gastro-enteritis, mastocytosis, Crohn's disease, colitis including ulcerative colitis, proctitis; coeliac disease, irritable bowel syndrome, and food-related allergies which may have effects remote from the gut, e.g. migraine, rhinitis or eczema.

According to other aspects, the present invention relates to the use of an inventive pharmaceutical composition in the preparation of a medicament for/in the treatment of above mentioned disorders or conditions.

According to another aspect, the present invention relates to a method of treating one or more of above mentioned disorders or conditions in a patient suffering from, or at risk of, said disease or condition, which comprises administering to the patient a therapeutically effective amount of an inventive pharmaceutical composition.

According to all aspects, the present invention further relates to combination therapies wherein one or more inventive crystal salt forms of sulfasalazine or the inventive pharmaceutical composition is administered concurrently (simultaneously) or sequentially or as a combined pharmaceutical preparation or as a combined administration schedule with one or more active ingredients (therapeutic agents) for the treatment of one or more of the diseases and conditions, preferably the diseases and conditions listed above.

In the context of the present specification, the term 'therapy' also includes 'prophylaxis' unless there are specific indications to the contrary. The terms 'therapeutic' and 'therapeutically' should be construed accordingly.

Prophylaxis is expected to be particularly relevant to the treatment of persons who have suffered a previous episode of, or are otherwise considered to be at increased risk of, the disease or condition in question. Persons at risk of developing a particular disease or condition generally include those having a family history of the disease or condition, or those who have been identified by genetic testing or screening to be particularly susceptible to developing the disease or condition.

According to the inventive treatment of the inflammatory diseases as set out hereinbefore, the sulfasalazine of the inventive pharmaceutical composition may be used in the same or separate pharmaceutical compositions with one, two, three or more active ingredients (therapeutic agents), preferably selected from the group consisting of therapeutic agents as listed below:

Non-steroidal anti-inflammatory agents (hereinafter NSAIDs) including non-selective cyclo-oxygenase COX-1/COX-2 inhibitors whether applied topically or systemically (such as piroxicam, diclofenac, propionic acids such as naproxen, flurbiprofen, fenoprofen, ketoprofen and ibuprofen, fenamates such as mefenamic acid, indomethacin, sulindac, azapropazone, pyrazolones such as phenylbutazone, salicylates such as aspirin); selective COX-2 inhibitors (such as meloxicam, celecoxib, rofecoxib, valdecoxib, lumarocoxib, parecoxib and etoricoxib); cyclo-oxygenase inhibiting nitric oxide donors (CINODs); glucocorticoids (whether administered by topical, oral, intramuscular, intravenous, or intra-articular routes); methotrexate, leflunomide, hydroxychloroquine, d-penicillamine; auranofin and other parenteral or oral gold preparations; analgesics; diacerein; intra-articular therapies such as hyaluronic acid derivatives; and nutritional supplements such as glucosamine.

Cytokine or agonist or antagonist of cytokine function, (including agents which act on cytokine signaling pathways such as modulators of the SOCS system) including alpha-, beta-, and gamma-interferons; insulin-like growth factor type I (IGF-I); interleukins (IL) including IL-1 to 23, and interleukin antagonists or inhibitors such as anakinra; tumour necrosis factor alpha (TNF-α) inhibitors such as anti-TNF monoclonal antibodies (for example infliximab, adalimumab, and golimumab) and TNF receptor antagonists including immunoglobulin molecules (such as etanercept) and low-molecular-weight agents such as pentoxyfylline.

Monoclonal antibody targeting B-Lymphocytes (such as CD20 (rituximab). MRA-alL16R and T-Lymphocytes, CTLA4-Ig, HuMax 11-15).

Modulator of chemokine receptor function such as an antagonist of CCR2, CCR2A, CCR2B, CCR3, CCR4, CCR5, CCR6, CCR7, CCR8, CCR9, CCRIO and CCRI I (for the C-C family); CXCRI, CXCR2, CXCR3, CXCR4 and CXCR5 (for the C-X-C family) and $CX_3CRI$ for the $C-X_3-C$ family.

Inhibitor of matrix metalloprotease (Tv-IMPs)$_5$ i.e., the stromefysins, the collagenases, and the gelatinases, as well as aggrecanase; especially collagenase-1 (MMP-I) 5 collagenase-2 (MMP-8), collagenase-3 (MMP-13), stromelysin-1 (MMP-3), stromelysin-2 (MMP-IO), and stromelysin-3 (MMP-11) and MMP-9 and MMP-12, including agents such as doxycycline.

Leukotriene biosynthesis inhibitor, 5-lipoxygenase (5-LO) inhibitor or 5-lipoxygenase activating protein (FLAP) antagonist such as; zileuton; ABT-761; fenleuton; tepoxalin; Abbott-79175; Abbott-85761; a N-(5-substituted)-thiophene-2-alkylsulfonamide; 2,6-di-tert-butylphenolhydrazones; a methoxytetrahydropyrans such as Zeneca ZD-213S; the compound SB-210661; a pyridinyl-substituted 2-cyanonaphthalene compound such as L-739,010; a 2-cyanoquinoline compound such as L-746,530; or an indole or quinoline compound such as MK-591, MK-886, and BAYx1005.

Receptor antagonist for leukotrienes (LT) B4, LTC4, LTD4, and LTE4, selected from the group consisting of the phenothiazin-3-Is such as L-651,392; amidino compounds such as CGS-25019c; benzoxalamines such as ontazolast; and compounds such as zafirlukast, ablukast, montelukast, pranlukast, verlukast (MK-679), RG-12525, Ro-245913, iralukast (CGP 45715A), and BAYx7195.

Phosphodiesterase (PDE) inhibitor such as a methylxanthanine including theophylline and aminophylline; a selective PDE isoenzyme inhibitor including a PDE4 inhibitor an inhibitor of the isoform PDE4D, such as apremilast or an inhibitor of PDE5.

Endothelin antagonist such as Tezosentan, Bosentan, Macitentan, Enrasentan, and Sixtasentan.

Angiotensin II antagonist such as Azilsartan, Losartan, Valsartan, Candesartan, and Telmisartan.

Dual antagonists for both angiotensin II and endothelin A receptors (DARAs), such as disclosed in WO2000001389 and WO2001044239.

Adenosine A2a agonist such as CGS-21680 and/or an adenosine A3 agonist such as IBMECA and/or an adenosine A2b antagonist. The present invention further relates to the combination of a compound of the invention, and a histamine type 1 receptor antagonist such as cetirizine, loratadine, desloratadine, fexofenadine, acrivastine, terfenadine, astemizole, azelastine, levocabastine, chlorpheniramine, promethazine, cyclizine, or mizolastine; applied orally, topically or parenterally.

Proton pump inhibitor (such as omeprazole) or a gastro-protective histamine type 2 receptor antagonist.

Antagonist of the histamine type 4 receptor.

Alpha-I/alpha-2 adrenoreceptor agonist vasoconstrictor sympathomimetic agent, such as propylhexedrine, phenylephrine, phenylpropanolamine, ephedrine, pseudoephedrine, naphazoline hydrochloride, oxymetazoline hydrochloride, tetrahydrozoline hydrochloride, xylometazoline hydrochloride, tramazoline hydrochloride or ethyl norepinephrine hydrochloride.

Anticholinergic agents including muscarinic receptor ($MI_5$ M2, and M3) antagonist such as atropine, hyoscine, glycopyrrolate, ipratropium bromide, tiotropium bromide, oxitropium bromide, pirenzepine or telenzepine.

Beta-adrenoceptor agonist (including beta receptor subtypes 1-4) such as isoprenaline, salbutamol, formoterol, salmeterol, terbutaline, orciprenaline, bitolterol mesylate, or pirbuterol, or a chiral enantiomer thereof.

Chromone, such as sodium cromoglycate or nedocromil sodium. The present invention still further relates to the combination of a compound of the invention, with a glucocorticoid, such as flunisolide, triamcinolone acetonide, betamethasone dipropionate, budesonide, fluticasone propionate, ciclesonide or mometasone furoate.

Agent that modulates a nuclear hormone receptor such as PPARs.

Immunoglobulin (Ig) or Ig preparation or an antagonist or antibody modulating Ig function such as anti-IgE (for example omalizumab).

Another systemic or topically-applied anti-inflammatory agent, such as thalidomide or a derivative thereof, a retinoid, dithranol or calcipotriol.

Aminosalicylates and sulfapyridines such as sulfasalazine, mesalazine, balsalazide, and olsalazine; and immunomodulatory agents such as the thiopurines, and corticosteroids such as budesonide. Preferably, the amount of further aminosalicylates and sulfapyridine are less than the amount of the inventive crystal forms of sulfasalazine per unit dosage form. Antibacterial agent such as a penicillin derivative, a tetracycline, a macrolide, a beta-lactam, a fluoroquinolone, metronidazole, an inhaled aminoglycoside; an antiviral agent including acyclovir, famciclovir, valaciclovir, ganciclovir, cidofovir, amantadine, rimantadine, ribavirin, zanamavir and oseltamavir; a protease inhibitor such as indinavir, nelfinavir, ritonavir, and saquinavir; a nucleoside reverse transcriptase inhibitor such as didanosine, lamivudine, stavudine, zalcitabine or zidovudine; or a non-nucleoside reverse transcriptase inhibitor such as nevirapine or efavirenz.

Cardiovascular agent such as a calcium channel blocker, a beta-adrenoceptor blocker, an angiotensin-converting enzyme (ACE) inhibitor, an angiotensin-2 receptor antagonist; a lipid lowering agent such as a statin or a fibrate; a modulator of blood cell morphology such as pentoxyfylline; thrombolytic, or an anticoagulant such as a platelet aggregation inhibitor.

Antidepressant (such as sertraline), an anti-Parkinsonian drug (such as deprenyl, L-dopa, ropinirole, pramipexole, a MAOB inhibitor such as selegine and rasagiline, a comP inhibitor such as tasmar, an A-2 inhibitor, a dopamine reuptake inhibitor, an NMDA antagonist, a nicotine agonist, a dopamine agonist or an inhibitor of neuronal nitric oxide synthase), or an anti-Alzheimer's drug such as donepezil, rivastigmine, tacrine, a COX-2 inhibitor, propentofylline or metrifonate.

Agent for the treatment of acute or chronic pain, such as a centrally or peripherally-acting analgesic (for example an opioid or derivative thereof), carbamazepine, phenytoin, sodium valproate, amitryptiline or other anti-depressant agent-s, paracetamol, or a non-steroidal anti-inflammatory agent.

A parenterally or topically-applied (including inhaled) local anaesthetic agent such as lignocaine or a derivative thereof.

anti-osteoporosis agent including a hormonal agent such as raloxifene, or a biphosphonate such as alendronate.

One or more agents selected from the following group: (i) tryptase inhibitor; (ii) platelet activating factor (PAF) antagonist; (iii) interleukin converting enzyme (ICE) inhibitor; (iv) IMPDH inhibitor; (v) adhesion molecule inhibitors including VLA-4 antagonist; (vi) cathepsin; (vii) kinase inhibitor such as an inhibitor of tyrosine kinase (such as Btk, Itk, Jak3 or MAP, for example Tofacitinib, Gefitinib or Imatinib mesylate), a serine/threonine kinase (such as an inhibitor of a MAP kinase such as p38, INK, protein kinase A, B or C, or inhibitors of kappaB kinases, such as $IKKI_5$ IKK2 or IKK3), or a kinase involved in cell cycle regulation (such as a cylin dependent kinase); (viii) glucose-6 phosphate dehydrogenase inhibitor; (ix) kinin-$B_1$—or $B_2$—receptor antagonist; (x) anti-gout agent, for example colchicine; (xi) xanthine oxidase inhibitor, for example allopurinol; (xii) uricosuric agent, for example probenecid, sulfinpyrazone or benzbromarone; (xiii) growth hormone secretagogue; (xiv) transforming growth factor (TGFβ); (xv) platelet-derived growth factor (PDGF); (xvi) fibroblast growth factor for example basic fibroblast growth factor (bFGF); (xvii) granulocyte macrophage colony stimulating factor (GM-CSF); (xviii) capsaicin cream; (xix) tachykinin KK. sub 1. or NK.sub3. receptor antagonist such as NKP-608C, SB-233412 (talnetant) or D-441S; (xx) elastase inhibitor such as LT-77 or ZD-0892; (xxi) TNF-alpha converting enzyme inhibitor (TACE); (xxii) induced nitric oxide synthase (iNOS) inhibitor; (xxiii) chemoattractant receptor-homologous molecule expressed on TH2 cells, (such as a CRTH2 antagonist); (xxiv) inhibitor of P38; (xxv) agent modulating the function of Toll-like receptors (TLR), (xxvi) agent modulating the activity of purinergic receptors such as P2X7; or (xxvii) inhibitor of transcription factor activation such as NFkB, API, or STATS, (xxvii) agents modulating guanylate cyclase such as riociguat (methyl-N-[4,6-Diamino-2-[1-[(2-fluorphenyl) methyl]-1H-pyrazolo[3,4-b]pyridin-3-yl]-5-pyrimidinyl]-N-methyl-carbaminat (IUPAC)).

One or more therapeutic agents for the treatment of cancer, preferably selected from the group consisting of (i) an antiproliferative/antineoplastic drug or a combination thereof, as used in medical oncology, such as an alkylating agent (for example cis-platin, carboplatin, cyclophosphamide, nitrogen mustard, melphalan, chlorambucil, busulphan or a nitrosourea); an antimetabolite (for example an antifolate such as a fluoropyrimidine like 5-fluorouracil, ortegafur, raltitrexed, methotrexate, cytosine arabinoside, hydroxyurea, gemcitabine or paclitaxel); an antitumour antibiotic (for example an anthracycline such as adriamycin, bleomycin, doxorubicin, daunomycin, epirubicin, idarubicin, mitomycin-C, dactinomycin or mithramycin); an antimitotic agent (for example a vinca alkaloid such as vincristine, vinblastine, vindesine or vinorelbine, or a taxoid such as taxol or taxotere): or a topoisomerase inhibitor (for example an epipodophyllotoxin such as etoposide, teniposide, amsacrine, topotecan or a camptothecin); (u) a cytostatic agent such as an antioestrogen (for example tamoxifen, toremifene, raloxifene, droloxifene or iodoxyfene), an oestrogen receptor down regulator (for example fulvestrant), an antiandrogen (for example bicalutamide, fhitamide, nilutamide or cyproterone acetate), a LHRH antagonist or LHRH agonist (for example goserelin, leuprorelin or biiserelin), a progestogen (for example megestrol acetate), an aromatase inhibitor (for example as anastrozole, letrozole, vorazole or exemestane) or an inhibitor of 5α-reductase such as finasteride; (iii) an agent which inhibits cancer cell invasion (for example a metalloproteinase inhibitor like marimastat or an inhibitor of urokinase plasminogen activator receptor function); (iv) an inhibitor of growth factor function, for example: a growth factor antibody (for example the anti-erbb2 antibody trastuzumab, or the anti-erbbI antibody cetuximab [C225]), a farnesyl transferase inhibitor, a tyrosine kinase inhibitor or a serine/threonine kinase inhibitor, an inhibitor of the epidermal growth factor family (for example an EGFR family tyrosine kinase inhibitor such as N-(3-chloro-4-fluorophenyl)-7-methoxy-6-(3-morpholinopropoxy)quinazolin-4-amine (gefitinib, AZDI 839), N-(3-ethynylphenyl)-6,7-bis(2-methoxyethoxy)quinazolin-4-amine (erlotinib. OSI-774) or 6-acrylamido-N-(3-chloro-4-fluorophenyl)-7-(3-morpholinopropoxy)quinazolin-4-amine (CI 1033)), an inhibitor of the platelet-derived growth factor family, or an inhibitor of the hepatocyte growth factor family; (v) an antiangiogenic agent such as one which inhibits the effects of vascular endothelial growth factor (for example the anti-vascular endothelial cell growth factor antibody bevacizumab, a compound disclosed in WO 97/22596, WO 97/30035, WO 97/32856 or WO 98/13354), or a compound that works by another mechanism (for example linomide, an inhibitor of integrin αvβ3 function or an angiostatin); (vi) a vascular damaging agent such as combretastatin A4, or a compound disclosed in WO 99/02166, WO 00/40529, WO 00/41669, WO 01/92224, WO 02/04434 or WO 02/08213; (vii) an agent used in antisense therapy, for example one directed to one of the targets listed above, such as ISIS 2503, an anti-ras antisense; (viii) an agent used in a gene therapy approach, for example approaches to replace aberrant genes such as aberrant p53 or aberrant BRCAI or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy; or (ix) an agent used in an immunotherapeutic approach, for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies.

One or more therapeutic agents for the treatment of airway disease, respiratory disease and/or an inflammatory disease such as for example chronic obstructive pulmonary disease and asthma. The inventive crystal salt forms of sulfasalazine can be administered by inhalation or by the oral route and the agent for the treatment of airway disease, respiratory disease and/or an inflammatory disease such as for example chronic obstructive pulmonary disease and asthma (other agent) can independently be selected to be administered by inhalation or by the oral route. The inventive crystal salt forms of sulfasalazine and the other agent may be administered in one pharmaceutical formulation or in separate pharmaceutical formulations. In case of separate pharmaceutical formulations, the inventive crystal salt forms of sulfasalazine and the other agent may be administered simultaneously or sequentially or separately.

Dependent on the therapeutic uses, the dosage of the inventive crystal salt forms of sulfasalazine will, of course, vary with the mode of administration, the treatment desired and the disorder indicated, but may typically be in the range from 1 mg/kg to 50 mg/kg.

EXAMPLES

The present invention is described in the following on the basis of exemplary embodiments, which merely serve as examples and which shall not limit the scope of the present protective right. The exemplified features may be combined separately or in any (sub)combination with the general disclosure of all aspects of the invention hereinbefore.

Example 1 Solubility of Sulfasalazine, Form A Meglumine Salt of Sulfasalazine and of Sulfasalazine in Pharmaceutical Compositions

HPLC

The amount of dissolved sulfasalazine was respectively determined by HPLC on an HP 1100 instrument, using a Waters X-Bridge 3.5 μm C18 column (150*4.6 mm) and a gradient method. The mobile phase consists of mobile phase (A): 1.13 g sodium dihydrogen phosphate and 2.5 g sodium acetate are dissolved in 1000 mL purified water. The pH is afterwards adjusted with acetic acid (100%) to 4.8. and mobile phase (B): 1 part mobile phase A is mixed with 4 parts of methanol for chromatography. The flow rate was 1.0 mL/min, injection volume 5 μL and detection wavelengths 320 nm (HP DAD series 1100). Run time is 10 min. Quantitation was performed using external standard methodology. The assay method has been validated with respect to selectivity, repeatability and linearity. Samples are prepared with dilute ammonia R3 PhEur.

Procedure A mg of sulfasalazine and Form A meglumine salt of sulfasalazine are respectively weighed into a 4 mL glass vial containing 2 mL water or FaSSIF-V2 medium and stirred at room temperature (20-25° C.) for 24 h, after which 20 mg of sulfasalazine and Form A meglumine salt were respectively additionally added until a saturated solution was obtained. The saturated solutions were filtrated using centrifuge filters (Nylon, 0.45 μM) and the clear supernatants were respectively injected either directly or after dilution with dilute ammonia R3 PhEur.

Procedure B

Sulfasalazine (1 g; 2.5 mmol) and meglumine (2 eq) were dissolved in water under magnetic stirring at room temperature until full dissolution. The resulting solution is further diluted with phosphate buffer (pH 6.8) to 1% v/v solution prior. The resulting phosphate buffer solution is diluted with dilute ammonia R3 prior to injection.

Procedure C

Kolliphor HS 15 (Solutol HS 15, Ph.Eur./USP, BASF with approx. 30% free propylenglycol), Kolliphor RH 40 (Cremophor RH 40, Ph.Eur./USP, BASF) and TPGS-1000 (USP, Antares Health Products) (2 g) were respectively dissolved in 20 mL water at approx. 60° C. To 10 mL of the subsequent respective solutions, 1000 mg sulfasalazine and 735 mg meglumine (1.5 eq) were added and stirred at room temperature for approx. 30 min. until sulfasalazine was respectively completely dissolved.

TABLE 1

| Group | Water | | FaSSIF-V2 | |
|---|---|---|---|---|
| | pH | Solubility (mg/mL) | pH | Solubility (mg/mL) |
| Active pharmaceutical ingredients (API): | | | | |
| sulfasalazine | 5.9 | 0.06 | 6.3 | 0.78 |
| Form A meglumine salt | 7.5 | 104.8 | 6.4 | 15.3 |
| | 6.0* | 60.3 | n.a. | n.a. |
| Pharmaceutical compositions: | | | | |
| Sulfasalazine (1 eq), meglumine (2 eq) | 6.0* | 174.3 | n.a. | n.a. |
| Sulfasalazine (10 w/v %), meglumine (7.2 w/v %), Kolliphor HS15 (10% w/v) | n.a. | 1.7 | n.a. | n.a. |
| Sulfasalazine (10 w/v %), meglumine (7.2 w/v %), Kolliphor RH40 (10% w/v) | n.a. | 1.6 | n.a. | n.a. |
| Sulfasalazine (10 w/v %), meglumine (7.2 w/v %), TPGS-1000 (10% w/v) | n.a. | 0.78 | n.a. | n.a. |

*diluted in phosphate Buffer pH 6.8

Example 2 Stability of Sulfasalazine in Pharmaceutical Compositions

HPLC

The amount of dissolved sulfasalazine was determined by HPLC on an HP 1100 instrument, using a Waters X-Bridge 3.5 μm C18 column (150*4.6 mm) and a gradient method. The mobile phase consists of mobile phase (A): 1.13 g sodium dihydrogen phosphate and 2.5 g sodium acetate are dissolved in 1000 mL purified water. The pH is afterwards adjusted with acetic acid (100%) to 4.8. and mobile phase (B): 1 part mobile phase A is mixed with 4 parts of methanol for chromatography. The flow rate was 1.0 mL/min, injection volume 5 μL and detection wavelengths 320 nm (HP DAD series 1100). Run time is 10 min. Quantitation was performed using external standard methodology. The assay method has been validated with respect to selectivity, repeatability and linearity. Samples are prepared with dilute ammonia R3 PhEur.

Procedure D

Kolliphor HS 15 (Solutol HS 15, Ph.Eur./USP, BASF with approx. 30% free propylenglycol), Kolliphor RH 40 (Cremophor RH 40, Ph.Eur./USP, BASF) and TPGS-1000 (USP, Antares Health Products) (2 g) were respectively dissolved in 20 mL water at approx. 60° C. To 10 mL of the respectively subsequent solutions, 1000 mg sulfasalazine and 735 mg meglumine (1.5 eq) were added and stirred at room temperature for approx. 30 min until sulfasalazine was respectively completely dissolved. The stability was tested over 2 weeks when stored at room temperature on a petri dish. Purity and content were tested immediately after manufacturing, after 24 and 48 hours and after 7 and 14 days. Sulfasalazine contents have been determined to a 100% sulfasalazine reference solution and purities are presented via area % related to initial values.

compartments) with 1.5 mL of DMEM culture medium. The cells were cultured at 37° C., 10% CO2 and 90% relative humidity in DMEM culture medium for 14 to 30 days until they formed confluent monolayers. Confluency and tightness of the cell monolayer were checked by measuring the transepithelial electrical resistance using an EVOM™ voltohmmeter with STX-2 electrode. Monolayers were rejected if the TEER was lower than 200 $\Omega*cm^2$ after pre-incubation (30 min) or after completion of the transport study. Test items were prepared according to the Biopharmaceutics Classification System (BCS) guidance. Experiments were performed in triplicate. Immediately prior to the transport experiment, the cells were washed twice with Krebs-Ringer and the buffer was then replaced by the transport solutions. After 30 min pre-incubation, samples were withdrawn from both donor and acceptor compartments. Six samples were taken in total at t=0, 30, 60, 90, 120 and 180 min. The efflux ratio is calculated as the $P_{app}$ (ba)/$P_{app}$ (ab), where $P_{app}$ (ba) is the apparent permeability coefficient for the transport of the test compound from the basal to the apical side (secretive direction) and the $P_{app}$ (ab) is the apparent permeability coefficient for the transport of the test compound from the apical to the basal side (absorptive direction). The apparent permeability coefficient $P_{app}$ (in cm/s) was calculated as the permeability rate at steady state (in ug/s)*(1/initial mass of test compound in donor compartment (in ug)*1/area of the exposed cell monolayer (in $cm^2$)*buffer volume of donor compartment (in $cm^3$).

Procedure E

The enteric coating from the commercially available pharmaceutical composition "sulfasalazine medac 500 mg EC" tablets was removed and the remaining core was pulverized and dissolved in water. The aqueous solution was further diluted with KRB to the desired concentrations.

Procedure F

Sulfasalazine (1 g; 2.5 mmol) alone or sulfasalazine (1 g; 2.5 mmol) and meglumine (1.5 eq) were respectively dissolved in water under magnetic stirring at room temperature until full dissolution. The resulting solution was further

TABLE 2

| Pharmaceutical composition | Purity (area %) | | | | |
| --- | --- | --- | --- | --- | --- |
| | 0 h | 24 h | 48 h | 7 d | 14 d |
| Sulfasalazine (10 w/v %), meglumine (7.2 w/v %), Kolliphor HS15 (10% w/v) | 97.2 | 97.3 | 97.3 | 97.2 | 97.2 |
| Sulfasalazine (10 w/v %), meglumine (7.2 w/v %), Kolliphor RH40 (10% w/v) | 97.2 | 97.3 | 97.3 | 97.2 | 97.2 |
| Sulfasalazine (10 w/v %), meglumine (7.2 w/v %), TPGS-1000 (10% w/v) | 97.2 | 97.3 | 97.3 | 97.2 | 97.1 |

Example 3 Comparison of Transport Rates of Sulfasalazine and Inventive Pharmaceutical Compositions Containing Sulfasalazine Across Caco 2 Cell Monolayer Caco-2 Mono Layers For the transport experiments, Caco-2 cells were seeded with a density of 67800 cells per square centimeter on Transwel™ filter inserts, which were placed into 12-well flat bottom cluster plates. The inserts (apical compartments) were supplied with 0.5 mL and the outer wells (basal diluted with Krebs-Ringer-Phosphate buffer (KRB) to the desired concentrations.

Procedure G

TPGS-1000 (USP, Antares Health Products) (1 g) was dissolved in 20 mL water at approx. 60° C. To 10 mL of the subsequent solution, 1000 mg sulfasalazine and 735 mg meglumine (1.5 eq) were added and stirred at room temperature for approx. 30 min until sulfasalazine was completely dissolved. The aqueous solutions are further diluted with KRB to the desired concentrations.

TABLE 3

Cumulative transport (μg/cm2) and $P_{app}$ values (E–06 cm/s) with relative standard deviations (RSD; %) after 180 min incubation of active ingredient sulfasalazine and sulfasalazine in pharmaceutical compositions as solutions in Krebs-Ringer buffer.

|  | Amount μg/mL | Transport direction | $P_{app}$ E–06 cm/s | RSD (%) | Cumulative drug transport μg/cm² | RSD (%) |
|---|---|---|---|---|---|---|
| API: |  |  |  |  |  |  |
| Sulfasalazine | 200 | ab | 1.16 | 35.8 | 3.81 | 35.1 |
|  |  | ba | 4.76 | 8.3 | 14.81 | 12.9 |
|  | 2000 | ab | 0.81 | 24.1 | 9.86 | 22.0 |
|  |  | ba | 2.79 | 4.6 | 32.07 | 1.9 |
| Pharmaceutical compositions: |  |  |  |  |  |  |
| Sulfasalazine medac 500 | 200 | ab | 1.36 | 17.2 | 5.82 | 3.3 |
|  | 2000 | ab | 1.71 | 21.3 | 48.60 | 17.2 |
| Sulfasalazine, meglumine (1.5 eq) | 200 | ab | 1.13 | 30.6 | 4.14 | 26.3 |
|  | 2000 | ab | 1.08 | 16.8 | 21.88 | 14.4 |
| Sulfasalazine (10 w/v %), meglumine (7.2 w/v %), TPGS-1000 (5 w/v %) | 200 | ab | 2.35 | 16.1 | 7.32 | 15.7 |
|  | 2000 | ab | 3.30 | 21.6 | 59.68 | 28.5 |

The ratio between the transport rates from ba to ab of the active pharmaceutical ingredient sulfasalazine ranges from 3.4 (2000 μg/mL) to 4.1 (200 μg/mL). The efflux ratio of the pharmaceutical composition containing 10 w/v % sulfasalazine with 7.2 w/v % meglumine and 5 w/v % TPGS-1000 ranges from 0.5 (200 μg/mL) to 1.2 (2000 μg/mL).

Example 4 Preparation of Crystal Salt Forms of Sulfasalazine 4.1 Preparation of D(−)-N-methylglucamine 2-hydroxy-5-[2-[4-[(2-pyridinylamino)sulfonyl]phenyl]diazenyl]-benzoate, crystal Form A Sulfasalazine (2.00 g, 5.0 mmol) and D(−)-N-methylglucamine (1.00 g, 5.1 mmol) were weighed into a 250 ml round-bottomed flask equipped with magnetic stirrer. Acetone (200 ml) was added and the mixture stirred at 60° C. The solid materials gradually dissolved and after a few hours a new precipitate started to form. The mixture was never completely dissolved. After 24 h at 60° C. tert-butyl methylether (40 ml) was added from a dropping funnel (5 min) and crystal seeds (1 mg Form A meglumine sulfasalazine salt obtained as described in Example 5) were added. After 30 min the heating was turned off and the mixture stirred another 60 h at ambient temperature. It was then filtered (Robu-Glas borosilicate glass filter porosity 3) and the solid washed with 20% mixture of tert-butyl methylether in acetone (50 ml). The material was dried 17 h in vacuo and weighed on the filter to give 2.92 g (97.4%) yellow crystalline powder. This material was analysed by 1H-NMR and found to contain 0.53% w/w acetone and traces of tert-butyl methylether (<0.02% w/w).

$^1$H NMR (400 MHz, DMSO-d6) δ 8.27 (d, J=2.7 Hz, 1H), 8.03-7.95 (m, 3H), 7.91-7.83 (m, 2H), 7.80 (dd, J=8.9, 2.7 Hz, 1H), 7.75 (ddd, J=8.9, 7.1, 1.9 Hz, 1H), 7.21 (d, J=8.7 Hz, 1H), 6.86 (t, J=6.6 Hz, 1H), 6.73 (d, J=8.9 Hz, 1H), 5.38 (s, 1H), 4.57 (s, 1H), 4.43 (s, 1H), 3.89-3.80 (m, 1H), 3.66 (dd, J=5.3, 1.6 Hz, 1H), 3.60 (dd, J=10.8, 3.2 Hz, 1H), 3.49 (dt, J=8.9, 4.2 Hz, 1H), 3.45-3.37 (m, 2H), 3.05 (dd, J=12.6, 3.3 Hz, 1H), 2.94 (dd, J=12.6, 9.5 Hz, 1H), 2.55 (s, 3H); $^{13}$C NMR (101 MHz, DMSO-d6) δ 170.96, 170.29, 154.12, 141.99, 127.70, 126.94, 126.78, 122.02, 119.07, 118.24, 71.28, 70.39, 70.10, 68.34, 63.27, 50.80; loss on drying (TGA; % w/w) is 0.2; melting point (DSC) is 163.5° C.±2.5° C. (onset); water vapor uptake (GVS; % w/w) at 30% RH is <0.4 and at 80% RH<0.9; solubility in de-ionized water at 24° C. and pH 6.6>54 mg/mL; stoichiometry, base to acid, of 1:1 was confirmed by NMR.

X-ray powder diffraction pattern of crystal Form A of the meglumine salt of sulfasalazine shown in FIG. 1, in particular comprising the following XRPD peaks (expressed as degrees 2θ±0.2 degrees)

(10) 6.35, 13.93 and 22.41, or
(11) 9.31, 15.86 and 20.99, or
(12) 6.35, 13.93, 15.48, 15.86, 22.41 and 23.60, or
(13) 6.35, 10.79, 12.93, 13.93, 15.48, 15.86, 18.12, 19.82 and 22.41, or
(14) 9.31, 10.79, 12.93, 13.93, 14.47, 15.48, 15.86, 17.56, 19.10, 23.60 and 28.07, or
(15) 6.35, 12.93, 13.93, 14.47, 15.48, 15.86, 19.10, 19.82, 20.99, 21.27, 22.41, 23.60, 23.89 and 28.07, or
(16) 6.35, 9.31, 10.79, 12.93, 13.93, 14.47, 15.48, 15.86, 17.78, 18.12, 19.82, 20.11, 20.99, 21.27, 22.41, 23.60, 23.89, 28.07 and 28.80, or
(17) 6.35, 9.31, 10.79, 12.93, 13.93, 14.47, 15.48, 15.86, 17.56, 17.78, 18.12, 18.50, 19.10, 19.82, 20.11, 20.99, 21.27, 22.41, 23.60, 23.89, 24.70, 25.14, 25.55, 25.93, 26.81, 28.07 and 28.80, or
(18) 6.35, 9.31, 10.79, 12.93, 13.93, 14.47, 15.48, 15.86, 17.56, 17.78, 18.12, 18.50, 19.10, 19.82, 20.11, 20.99, 21.27, 22.41, 23.60, 23.89, 24.70, 25.14, 25.55, 25.93, 26.81, 28.07, 28.80, 29.49, 32.01, 32.58, 33.23.

4.2 Preparation of D(−)-N-methylglucamine 2-hydroxy-5-[2-[4-[(2-pyridinylamino)sulfonyl]phenyl]diazenyl]-benzoate, crystal Form A To a suspension of 30 mg sulfasalazine in acetone the equimolar amount of D(−)-N-methylglucamine (1 M stock solution in water) was added. The suspension was heated to 23° C. and the resulting solution stirred for 4 days, after which the solvent was slowly evaporated. The salt product was washed and filtered to dryness, yielding the polymorph named form A D(−)-N-methylglucamine 2-hydroxy-5-[2-[4-[(2-pyridinylamino)sulfonyl]phenyl]diazenyl]-benzoate.

$^1$H-NMR (400 MHz, DMSO-$d_6$) δ 8.27 (d, J=2.7 Hz, 1H), 8.05-7.95 (m, 3H), 7.91-7.83 (m, 2H), 7.80 (dd, J=8.8, 2.7 Hz, 1H), 7.75 (ddd, J=8.9, 7.2, 1.9 Hz, 1H), 7.21 (d, J=8.7 Hz, 1H), 6.86 (t, J=6.6 Hz, 1H), 6.73 (d, J=8.8 Hz, 1H), 5.37 (s, 1H), 4.57 (s, 1H), 4.44 (s, 1H), 3.88-3.80 (m, 1H), 3.66 (dd, J=5.2, 1.6 Hz, 1H), 3.60 (d, J=10.7 Hz, 1H), 3.53-3.37 (m, 3H), 3.05 (dd, J=12.6, 3.4 Hz, 1H), 2.94 (dd, J=12.6, 9.5 Hz, 1H), 2.56 (s, 3H); $^{13}$C-NMR (101 MHz, DMSO-$d_6$) □ 171.01, 170.25, 154.13, 141.97, 127.70, 126.93, 126.78, 122.01, 119.06, 118.25, 71.28, 70.38, 70.09, 68.31, 63.26, 50.78, 40.12, 33.04; melting point (DSC): 160° C.±2° C. (onset); water vapor uptake (GVS; % w/w) at 30% RH is 0.4; at 80% RH is 1.1; stoichiometry, base to acid, of 1:1 was confirmed by NMR and HPLC.

X-ray powder diffraction pattern of crystal Form A of the meglumine salt of sulfasalazine shown in FIG. 1, in particular comprising the following XRPD peaks (expressed as degrees 2θ±0.2 degrees)
  (1) 6.35, 13.93 and 22.41, or
  (2) 9.31, 15.86 and 20.99, or
  (3) 6.35, 13.93, 15.48, 15.86, 22.41 and 23.60, or
  (4) 6.35, 10.79, 12.93, 13.93, 15.48, 15.86, 18.12, 19.82 and 22.41, or
  (5) 9.31, 10.79, 12.93, 13.93, 14.47, 15.48, 15.86, 17.56, 19.10, 23.60 and 28.07, or
  (6) 6.35, 12.93, 13.93, 14.47, 15.48, 15.86, 19.10, 19.82, 20.99, 21.27, 22.41, 23.60, 23.89 and 28.07, or
  (7) 6.35, 9.31, 10.79, 12.93, 13.93, 14.47, 15.48, 15.86, 17.78, 18.12, 19.82, 20.11, 20.99, 21.27, 22.41, 23.60, 23.89, 28.07 and 28.80, or
  (8) 6.35, 9.31, 10.79, 12.93, 13.93, 14.47, 15.48, 15.86, 17.56, 17.78, 18.12, 18.50, 19.10, 19.82, 20.99, 21.27, 22.41, 23.60, 23.89, 24.70, 25.14, 25.55, 25.93, 26.81, 28.07 and 28.80, or
  (9) 6.35, 9.31, 10.79, 12.93, 13.93, 14.47, 15.48, 15.86, 17.56, 17.78, 18.12, 18.50, 19.10, 19.82, 20.11, 20.99, 21.27, 22.41, 23.60, 23.89, 24.70, 25.14, 25.55, 25.93, 26.81, 28.07, 28.80, 29.49, 32.01, 32.58, 33.23.

4.3 Preparation of piperazine 2-hydroxy-5-[2-[4-[(2-pyridinylamino)sulfonyl]phenyl]diazenyl]-benzoate, crystal Form A To a suspension of 30 mg sulfasalazine in methanol the equimolar amount of piperazine (1 M stock solution in water) was added. The suspension was heated to 23'C and stirred for 4 days. The salt product was then filtered, washed and filtered again to dryness, yielding the polymorph named Form A piperazine sulfasalazine.

$^1$H-NMR (400 MHz, DMSO-$d_6$) δ 8.28 (d, J=2.7 Hz, 1H), 8.00 (dt, J=6.9, 2.1 Hz, 3H), 7.88 (d, J=8.6 Hz, 2H), 7.84 (dd, J=8.8, 2.7 Hz, 1H), 7.75 (ddd, J=8.9, 7.2, 1.9 Hz, 1H), 7.21 (d, J=8.7 Hz, 1H), 6.86 (t, J=6.4 Hz, 1H), 6.79 (d, J=8.8 Hz, 1H), 3.18 (s, 8H); $^{13}$C-NMR (101 MHz, DMSO-$d_6$) □ 170.55, 169.77, 154.01, 142.36, 127.71, 127.22, 126.65, 122.10, 118.49, 118.22, 41.14; melting point (DSC): 270° C.±2° C. (heat rate 100 K/min); water vapor uptake (GVS; % w/w) at 30% RH is 0.4; at 80% RH is 0.9; solubility in de-ionized water at 24° C. after 24 h: 0.12 mg/mL; stoichiometry, base to acid, of 1:2 was confirmed by NMR and HPLC.

X-ray powder diffraction pattern of crystal Form A of the piperazine salt of sulfasalazine shown in FIG. 2, in particular comprising the following XRPD peaks (expressed as degrees 2θ±0.2 degrees)
  (1) 11.95, 12.30 and 16.42, or
  (2) 12.30, 12.93 and 15.00, or
  (3) 11.95, 12.30, 12.93, 16.42, 17.87 and 20.36, or
  (4) 8.11, 11.95, 12.30, 15.01, 16.42, 17.87, 20.36 and 20.74, or
  (5) 11.95, 12.30, 12.93, 15.01, 16.42, 17.87, 20.36, 20.74, 22.41 and 23.41 or
  (6) 11.95, 15.01, 16.42, 17.87, 20.36, 20.74, 23.41, 24.01, 24.67, 24.99 and 26.09, or
  (7) 8.11, 11.95, 12.30, 12.93, 15.01, 16.42, 17.87, 20.36, 20.74, 22.41, 23.41, 24.01, 24.67, 24.99 and 26.09, or
  (8) 11.95, 12.30, 12.93, 15.01, 16.42, 17.87, 20.36, 20.74, 22.41, 23.41, 24.01, 24.67, 24.99, 26.09, 26.81, 27.73 and 28.80, or
  (9) 8.11, 11.95, 12.30, 12.93, 15.01, 16.42, 17.87, 20.36, 20.74, 22.41, 23.41, 24.01, 24.67, 24.99, 26.09, 26.81, 27.73, 28.80, 29.80 and 30.43.

4.4 Preparation of diethylamine 2-hydroxy-5-[2-[4-[(2-pyridinylamino)sulfonyl]phenyl]diazenyl]-benzoate, crystal Form A To a suspension of 30 mg sulfasalazine in acetonitrile the equimolar amount of diethylamine (1 M stock solution in water) was added. The suspension was heated to 23° C. and stirred for 4 days. The salt product was then filtered, washed and filtered again to dryness, yielding the polymorph named form A diethylamine sulfasalazine.

$^1$H-NMR (400 MHz, DMSO-$d_6$) δ 8.26 (d, J=2.7 Hz, 1H), 8.02-7.95 (m, 3H), 7.87 (d, J=8.3 Hz, 2H), 7.79 (dd, J=8.9, 2.7 Hz, 1H), 7.75 (t, J=8.7, 7.6 Hz, 1H), 7.21 (d, J=8.6 Hz, 1H), 6.86 (s, 1H), 6.72 (d, J=8.8 Hz, 1H), 2.93 (q, J=7.3 Hz, 4H), 1.16 (t, J=7.3 Hz, 6H); $^{13}$C-NMR (101 MHz, DMSO-$d_6$) □ 170.21, 141.91, 126.91, 126.79, 121.99, 119.06, 118.27, 41.35, 11.05; melting point (DSC): 200° C.±2° C. (heat rate 10 K/min); water vapor uptake (GVS; % w/w) at 30% RH is 0.3; at 80% RH is 0.5; solubility in de-ionized water at 24° C. after 24 h: >0.31 mg/mL; stoichiometry, base to acid, of 1:1 was confirmed by NMR and HPLC.

X-ray powder diffraction pattern of crystal Form A of the diethylamine salt of sulfasalazine shown in FIG. 3, in particular comprising the following XRPD peaks (expressed as degrees 2θ±0.2 degrees)
  (1) 7.16, 11.48, and 18.78, or
  (2) 10.50, 15.41 and 21.87, or
  (3) 7.16, 10.50, 11.48, 18.78, 21.65 and 21.87, or
  (4) 10.50, 11.48, 12.42, 14.38, 15.41, 16.64, 18.78 and 21.87, or
  (5) 7.16, 10.50, 11.01, 11.48, 13.87, 15.92, 16.64, 18.78, 21.08, 21.65 and 22.15, or
  (6) 7.16, 10.50, 11.01, 11.48, 12.42, 13.87, 14.38, 15.41, 15.92, 16.64, 17.19, 18.28, 18.78, 21.08, 21.65, 21.87, and 22.15 or
  (7) 7.16, 10.50, 11.48, 12.42, 13.87, 14.38, 15.41, 15.92, 16.64, 20.52, 21.08, 21.65, 21.87, 22.15, 22.47, 23.16, 23.63, 24.14 and 25.11, or
  (8) 7.16, 10.50, 11.01, 11.48, 12.42, 13.87, 14.38, 15.41, 15.92, 16.64, 17.19, 18.28, 18.78, 21.08, 21.65, 21.87, 22.15, 22.47, 23.16, 23.63, 24.14 and 25.11, or
  (9) 7.16, 10.50, 11.01, 11.48, 12.42, 13.87, 14.38, 15.41, 15.92, 16.64, 17.19, 18.28, 18.78, 21.08, 21.65, 21.87, 22.15, 22.47, 23.16, 23.63, 24.14, 25.11, 26.94, 27.95, 28.92, 29.46.

4.5 Preparation of diethylamine 2-hydroxy-5-[2-[4-[(2-pyridinylamino)sulfonyl]phenyl]diazenyl]-benzoate, crystal Form B 25 mg sulfasalazine was added to 5 ml acetone was added and a solution containing 10% excess of the counter ion diethylamine in acetone was added. The mixture was heated to 45° C., and the solvent slowly evaporated, resulting in the polymorph named Form B diethylamine sulfasalazine salt.

X-ray powder diffraction pattern of crystal Form B of the diethylamine salt of sulfasalazine shown in FIG. 4, in particular comprising the following XRPD peaks (expressed as degrees 2θ±0.2 degrees)
(1) 6.85, 17.82 and 22.75, or
(2) 11.38, 20.58 and 23.98, or
(3) 6.85, 11.38, 17.82, 20.58 and 22.75, or
(4) 6.85, 11.38, 11.70, 17.62, 20.58, 22.75 and 23.98, or
(5) 11.38, 11.70, 15.29, 16.71, 17.62, 19.92, 20.58, 21.30, 22.75, 23.63 and 23.98, or
(6) 6.85, 11.38, 11.70, 14.78, 15.29, 15.70, 16.71, 17.62, 19.92, 20.20, 20.58, 21.30, 22.75, 23.63, 23.98 and 28.61 or
(7) 6.85, 11.38, 11.70, 14.78, 15.29, 15.70, 16.71, 17.62, 19.92, 20.20, 20.58, 21.30, 22.75, 23.63, 23.98, 25.05, 25.71, 26.81, 27.95 and 28.61, or
(8) 6.85, 11.38, 11.70, 14.78, 15.29, 15.70, 16.71, 17.62, 19.92, 20.20, 20.58, 21.30, 22.75, 23.63, 23.98, 25.05, 25.71, 26.81, 27.95, 28.61, 29.14, 31.06.

The invention claimed is:

1. A pharmaceutical composition for oral administration comprising:
(I) 2-hydroxy-5-[2-[4-[(2-pyridinylamino)sulfonyl]phenyl]diazenyl]-benzoic acid (sulfasalazine) and/or as sulfasalazine organic salt, the process comprising of the following steps:
A: Providing sulfasalazine,
B: Providing an organic amine containing constituent;
C: Providing one or more pharmaceutical excipients and optionally one or more further active ingredients,
D: Mixing a therapeutically effective amount of sulfasalazine of step A) with a suitable amount of the organic amine containing constituent of step B) and the one or more pharmaceutical excipients and optionally one or more further active ingredient of step C) to form the pharmaceutical composition for oral administration,
wherein the organic amine containing constituent does not represent Tris(hydroxymethyl)aminomethane, and
(II) one or more active ingredients of the further pharmaceutical compositions are selected from the group consisting of a non-steriodal anti-inflammatory agents; a non-selective cyclo-oxygenase COX-1/COX-2 inhibitor a propionic acid, a fenamate, indomethacin, sulindac, ayapropayone, a pyrayoleone, a salicylate, a selective COX-2 inhibitor, a cyclo-oxygenase inhibiting nitric oxide donor (CINODs); glucocorticoid, triamcinolone acetonide, betamethasone dipropionate, budesonide, fluticasone propionate, ciclesonide or mometasone furoate; methotrexate; leflunomide; hydroxychloroquine; d-penicillamine; diacerein; a nutritional supplement; a gold preparation; a cytokine or agonist or antagonist of cytokine function; a monoclonal antibody targeting B-Lymphocyte; MRA-aIL16R; a T-lymphocyte; CTLA4-Ig; HuMax 11-15; a modulator of chemokine receptor function; azathioprine, tofacitinib, a monoclonal antibodie and an interleukin 1 receptor antagonist.

2. The pharmaceutical composition of claim 1, in the form of a solid pharmaceutical composition or a liquid pharmaceutical composition.

3. The pharmaceutical composition according to claim 1, wherein the sulfasalazine comprises an organic sulfasalazine salt.

4. The pharmaceutical composition of claim 1, wherein the sulfasalazine is present in the therapeutically effective dose amount of sulfasalazine per dose of the pharmaceutical composition for oral administration range from 10 mg to 2,000 mg.

5. A method of treating
i) A human disease or condition in which modulation of inflammatory cells is beneficial, or
ii) A disease or condition concerning bones or joints; or
iii) A disease or condition concerning gastro-intestinal tract or a food-related allergy which may have effects remote from the gut, in a patient suffering from, or at risk of, said disease or condition, which comprises administering to the patient a pharmaceutical composition according to claim 1.

6. The method according to claim 5, wherein the pharmaceutical composition is sequentially or concurrently co-administered with one or more further pharmaceutical compositions, wherein one or more active ingredients of the further pharmaceutical compositions are selected from the group consisting of a non-steriodal anti-inflammatory agent, a propionic acid, a fenamate, indomethacin, sulindac, ayapropayone, pyrayoleone, a salicylates, a selective COX-2 inhibitor, a cyclo-oxygenase inhibiting nitric oxide donor (CINODs); glucocorticoid, triamcinolone acetonide, betamethasone dipropionate, budesonide, fluticasone propionate, ciclesonide or mometasone furoate; methotrexate; leflunomide; hydroxychloroquine; d-penicillamine; diacerein; a nutritional supplements; a cytokine or agonist or antagonist of cytokine function; a monoclonal antibody targeting B-Lymphocytes, MRA-aIL16R; a T-lymphocyte; CTLA4-Ig; HuMax 11-15; a modulator of chemokine receptor function, azathioprine, tofacitinib, a monoclonal antibody; and an interleukin 1 receptor antagonist.

7. The pharmaceutical composition of claim 1, wherein the organic amine containing constituent is selected from meglumine piperazine and diethylamine.

8. The pharmaceutical composition of claim 1, wherein the one or more active ingredients of the further pharmaceutical compositions are preferably selected from the group consisting of piroxicam, diclofenac, naproxen, flurbiprofen, fenoprofen, ketoprofen, ibuprofen, mefenamic acid, phenylbutazone, aspirin, meloxicam, celecoxib, rofecoxib, valdecoxib, lumarocoxib, parecoxib, etoricoxib, flunisolide, glucosamine; auranofin; CD20 (rituximab); an antagonist of CCR2, CCR2A, CCR2B, CCR3, CCR4, CCR5, CCR6, CCR7, CCR8, CCR9, CCRIO and CCRI 1 (for the C-C family), CXCR1, CXCR2, CXCR3, CXCR4 and CXCR5 (for the C-X-C family) and CX3CR1 (for the C-X3-C family); the anti tumour necrosis factor alpha monoclonal antibodies infliximab, adalimumab, and golimumab; anakinra; etanercept, and abatacept; more preferably methotrexate and hydroxychloroquine.

9. The prepared pharmaceutical composition of claim 2, wherein the solid pharmaceutical composition is the form selected from the group consisting of a granule, a multiple unit pellets system (MUPS), a tablet, multiple unit pellet tablets (MUP tablets), a capsule, and a powder; a syrup and a suspension.

10. The pharmaceutical composition of claim 1, wherein the therapeutically effective dose is selected from the group consisting of 10 mg, 20 mg, 25 mg, 30 mg, 40 mg, 50 mg, 60 mg, 70 mg, 75 mg, 80 mg, 90 mg, 100 mg, 110 mg, 120 mg, 125 mg, 130 mg, 140 mg, 150 mg, 160 mg, 170 mg, 175 mg, 180 mg, 190 mg, 200 mg, 210 mg, 220 mg, 225 mg, 230 mg, 240 mg, 250 mg, 260 mg, 270 mg, 275 mg, 280 mg, 290 mg, 300 mg, 310 mg, 320 mg, 325 mg, 330 mg, 340 mg, 350 mg, 360 mg, 370 mg, 375 mg, 380 mg, 390 mg, 400 mg, 410 mg, 420 mg, 425 mg, 430 mg, 440 mg, 450 mg, 460 mg, 470 mg, 475 mg, 480 mg, 490 mg, 500 mg, 525 mg, 550 mg, 575 mg, 600 mg, 625 mg, 650 mg, 675 mg, 700 mg, 725 mg, 750 mg, 775 mg, 800 mg, 825 mg, 850 mg, 875 mg, 900 mg, 925 mg, 950 mg, 975 mg, 1,000 mg, 1,025 mg, 1,050 mg, 1,075 mg, 1,100 mg, 1,125 mg, 1,150 mg, 1,175 mg, 1,200 mg, 1,225 mg, 1,250 mg, 1,275 mg, 1,300 mg, 1,325 mg, 1,350 mg, 1,375 mg, 1,400 mg, 1,425 mg, 1,450 mg, 1,475 mg, 1,500 mg, 1,525 mg, 1,550 mg, 1,575 mg, 1,600 mg, 1,625 mg, 1,650 mg, 1,675 mg, 1,700 mg, 1,725 mg, 1,750 mg, 1,775 mg, 1,800 mg, 1,825 mg, 1,850 mg, 1,875 mg, 1,900 mg, 1,925 mg, 1,950 mg, 1,975 mg, and 2,000 mg.

11. A method of claim 5, wherein the disease condition is selected from the group consisting of osteoarthritis/osteoarthrosis, both primary and secondary to congenital hip dysplasia; cervical and lumbar spondylitis, low back and neck pain; rheumatoid arthritis and Still's disease; ankylosing spondylitis, psoriatic arthritis, reactive arthritis and undifferentiated spondarthropathy, septic arthritis and other infection-related arthopathies and bone disorders, tuberculosis, Potts' disease and Poncet's syndrome; acute and chronic crystal-induced synovitis, urate gout, calcium pyrophosphate deposition disease, and calcium apatite related tendon, bursal and synovial inflammation; Behcet's disease; primary and secondary Sjogren's syndrome; systemic sclerosis and limited scleroderma; systemic lupus erythematosus, mixed connective tissue disease, and undifferentiated connective tissue disease; inflammatory myopathies, dermatomyositis and polymyositis; polymyalgia rheumatic; juvenile arthritis including idiopathic inflammatory arthritis of joint distribution and associated syndromes, rheumatic fever and its systemic complications; vasculitis, giant cell arteritis, Takayasu's arteritis, Churg-Strauss syndrome, polyarteritis nodos, microscopic polyarteritis, and vasculitis associated with viral infection, hypersensitivity reactions, cryoglobulins, and paraproteins; Familial Mediterranean fever, Muckle-Wells syndrome, and Familial Hibernian Fever, Kikuchi disease; drug-induced arthralgias, tendonitis, and myopathies.

12. The method of claim 4, wherein the disease or condition is selected from the group consisting of eosinophilic gastro-enteritis, mastocytosis, Crohn's disease, colitis, ulcerative colitis, proctitis; coeliac disease and irritable bowel syndrome.

13. The method of claim 4, wherein the disease or condition is selected from the group consisting of migraine, rhinitis and eczema.

14. The method according to claim 5, wherein the one or more active ingredients of the further pharmaceutical compositions are selected from the group consisting of a non-selective cyclo-oxygenase COX-1/COX-2 inhibitor, piroxicam, diclofenac, naproxen, flurbiprofen, fenoprofen, ketoprofen, ibuprofen, mefenamic acid, phenylbutazone, aspirin, meloxicam, celecoxib, rofecoxib, valdecoxib, lumarocoxib, parecoxib and etoricoxib, flunisolide, a glucosamine; a gold preparation, auranofin; CD20 (rituximab); an antagonist of CCR2, CCR2A, CCR2B, CCR3, CCR4, CCR5, CCR6, CCR7, CCR8, CCR9, CCR1O and CCRI I (for the C-C family), CXCR1, CXCR2, CXCR3, CXCR4 and CXCR5 (for the C-X-C family) and CX3CR1 (for the C-X3-C family); am anti tumour necrosis factor alpha monoclonal antibody infliximab, adalimumab, golimumab; anakinra; etanercept, abatacept; methotrexate and hydroxychloroquine.

\* \* \* \* \*